United States Patent [19]

Cooper et al.

[11] Patent Number: 4,642,284
[45] Date of Patent: Feb. 10, 1987

[54] METHOD AND SYSTEM FOR DETECTION OF COMPLEMENT PATHWAY ACTIVATION

[75] Inventors: Neil Cooper, San Diego; James T. Mayes, La Jolla, both of Calif.

[73] Assignee: Scripps Clinic and Research Foundation, La Jolla, Calif.

[21] Appl. No.: 503,705

[22] Filed: Jun. 13, 1983

[51] Int. Cl.$^4$ .................... G01N 53/00; G01N 33/563
[52] U.S. Cl. .......................................... 435/7; 435/4; 435/28; 436/512; 436/518; 436/520; 436/528; 436/529; 436/530; 436/536; 436/538; 436/540; 436/543; 436/544; 436/547; 436/821
[58] Field of Search .................... 436/821, 540, 7, 512

[56] References Cited

U.S. PATENT DOCUMENTS

| | | | |
|---|---|---|---|
| 4,298,592 | 11/1981 | Lin et al. | 436/540 |
| 4,342,566 | 8/1982 | Theofilopoulos. | |
| 4,343,896 | 8/1982 | Wolters et al. | 436/540 |
| 4,376,110 | 3/1983 | David et al. | 436/540 |

OTHER PUBLICATIONS

Natelson et al.—Clinical Immunochemistry (1978) pp. 108–111 (Publisher Am. Assn. Clin. Chem.).
Harpel et al., Clinical Research 30:563A (1982).
Cooper et al., Springer Semin. Immunopathol. 6:195–212 (1983).
Chapter entitled "The Complement System" pp. 124–135 of Basic and Clinical Immunology. (4th ed. 1982).
Bergen et al., Molecular Immunology 19:857–864 (1982).
Chapter entitled "Laboratory Evaluation of Complement Activation" pp. 393–410 from Immunoassays: Clinical Laboratory Techniques for the 1980's (1980).
Hack et al., Journal of Immunology 127: 1450–1453 (1981).

*Primary Examiner*—Sam Rosen
*Attorney, Agent, or Firm*—Dressler, Goldsmith, Shore, Sutker & Milnamow, Ltd.

[57] ABSTRACT

A method and system for detecting and preferably measuring the presence of an activated complement complex in a sample is discussed. The presence of such an activated complex is indicative of complement pathway activation and includes a first complement component and a second complement component. The method uses a first binding agent specific to the first complement component and a second binding agent specific to the second complement component which when bound with the complex forms an aggregate. The second specific binding agent includes a label whose presence is used to detect and measure the amount of aggregate and therefore activated complex in a sample. An assay system and aggregate for use in an assay system are also discussed.

56 Claims, 12 Drawing Figures

METHOD AND SYSTEM FOR DETECTION OF COMPLEMENT PATHWAY ACTIVATION

The U.S. Government has rights in this invention pursuant to grants awarded by the U.S. Public Health Service.

TECHNICAL FIELD OF THE INVENTION

The present invention relates to the detection and measurement complement pathway activation by to the presence of an activated complex in a sample.

BACKGROUND OF THE INVENTION

The complement system is a complex group of proteins in body fluids that, working together with antibodies or other factors, play an important role as mediators of immune, allergic, immunochemical and immunopathological reactions. Activation of the complement system can result in a wide range of reactions such as lysis of various kinds of cells, bacteria and protozoa, inactivation of viruses, and the direct mediation of inflammatory processes. Through the hormone-like activity of several of its components, the complement system can recruit and enlist the participation of other humoral and cellular effector systems. These in turn can induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. Many of these proteins when activated combine with some of the other proteins to form enzymes to cleave and activate still other proteins in the system. The sequential activation of these proteins follows two main pathways, the classical pathway and the alternative pathway. Both pathways use a common terminal trunk which leads to cell lysis or virus inactivation.

The classical pathway can be activated by antigen-antibody complexes, aggregated immunoglobulins and non-immunological substances such as DNA and trypsin-like enzymes. The classical pathway of activation involves, successively, four components denominated C1, C4, C2 and C3. These components can be grouped into two functional units: C1 or recognition unit; and C4, C2, and C3 or activation unit. Five additional components denominated C5, C6, C7, C8, and C9 define the membrane attack unit forming the terminal truck common to both pathways.

In the classical pathway, C1 is activated such as by attachment to an immunoglobulin and through a series of reactions produces an activated $\overline{C1s}$ from a constituent of C1. A bar over the term for a complement factor denotes an active enzyme. Activated $\overline{C1s}$ cleaves portions of both of components C4 and C2. Parts of the C4 and C2 components then combine to form the activated complex $\overline{C4b,2a}$ having a molecular weight of about 280,000. $\overline{C4b,2a}$ is a proteolytic enzyme which continues ongoing complement action. Earlier components are no longer required after it has been formed. $\overline{C4b,2a}$ cleaves and thereby activates the next component of the sequence, C3, to produce C3b which attaches to cell membranes adjacent to the $\overline{C4b,2a}$. The C3b then combines with the $\overline{C4b,2a}$ to form the last activated complex in the classical pathway $\overline{C4b,2a,3b}$. This enzyme cleaves C5, a component of the membrane attack unit.

The alternative pathway, also known as the properdin pathway, comprises at least six components. Five of these components truly belong to the alternative pathway, factors B, D, properdin (P), and two inhibitors, H and I. The sixth component, C3, can also be found in the classical pathway. Component C3b is sometimes also known as factor A. The alternative pathway can be activated by immunological substances such as IgA and nonimmunological substances such as certain complex polysacharides, trypsin-like enzymes and cobra venom factor. Even in the absence of any antibody or immunoglobulin, the alternative pathway can destroy microorganisms.

Activation of the alternative pathway proceeds in a different manner than the classical pathway. An initial requirement is the presence of C3b which appears to be continuously generated in small amounts in the body. C3b production is thought to be due to water induced cleavage of a thioester bond in C3 forming an activated C3* which reacts with the factors B and D to generate an enzyme to cleave C3 into C3a and C3b. C3b can be further produced by a positive feedback mechanism in which factor D and Bb (a component of factor B) combine with C3b to form the activated complex $\overline{C3b,Bb}$ that acts as an enzyme in an amplification loop to cleave more C3 to form additional C3b. Factors I and H act as regulator proteins by cleaving C3b to render it inactive. Other regulator proteins include C1 inhibitor and C4 binding protein.

C3b,Bb enzyme molecules are rendered more efficient by properdin (P) which binds to the complex and stabilizes it by slowing the spontaneous disociation of factor Bb. Both $\overline{C3b,Bb}$ and $\overline{C3b,P,Bb}$ cleave additional C3 molecules to form modified poly-C3b enzymes, $\overline{C3b_n,Bb}$ and $\overline{C3b_n,P,Bb}$, wherein "n" is greater than 1. Any of these molecules can also cleave C5 into C5a and C5b and initate the membrane attack unit of the same common terminal trunk. The C5b then combines with C6 and C7 to form an active trimolecular complex, C5b,6,7. The C5b,6,7 then combines with C8 and a plurality of C9's to form a further, active complex, which on the surface of a cell causes cytolysis.

Study and measurement of the activation of a complement pathway can provide an indication of many possible biological disorders. The two complement pathways have been implicated in the pathogenesis or symptomatology of a broad spectrum of human diseases and pathologic conditions. In the case of the classical pathway, these include immune complex diseases of several types, autoimmune diseases, in particular systemic lupus erythematosus, and infectious diseases. The alternative pathway has been found to be involved in infections with gram negative bacteria, viruses, parasites, and fungi, gram negative septicemia, and various dermatologic, renal, and hematologic diseases. Alternative pathway activation has also been associated with trauma, burns and adult respiratory distress syndrome (ARDS), as well as contact with dialysis membranes such as during hemodialysis and cardiac bypass surgery. In vitro studies have indicated that a number of gram negative bacteria and bacterial products, virus infected cells, viruses, protozoa, fungi, burns, damaged and injured cells, and other substances of biomedical importance have the ability to activate the alternative pathway in human serum.

Present methods to assess and quantitify complement pathway function and activation are indirect, limited in number, and generally only available in laboratories engaged in research on the complement pathways. They measure not the dynamic activity of a pathway, but rather a static end state or the capability of the pathway. One such crude screening test for an intact complement sequence in human serum is hemolytic assay. Hemolytic assay is used to calculate the CH50 level, the point at which 50 percent of the antibody-coated erythrocytes (EA) in a test sample are lysed by a particular dilution of serum containing the complement components. This method is rather insensitive because it relies on a secondary event, lysis, and does not measure pathway activation directly, but rather residual functional activity of the complement system. Hemolytic assay also cannot measure the activity of any particular component produced in the activation sequence, only the total activation. Activation and, by implication, functional ability of the entire complement sequence are necessary to result in lysis.

The presence of individual complement components in blood sera can be measured by the use of antibodies prepared against the appropriate complement component. However, this only gives an indication of the amount of complement component present in sera and not the amount of activation of a pathway. Previous attempts to measure the presence of only an activated component require complicated separation techniques. See Cooper, "Laboratory Evaluation of Complement Activation" in *Immunoassays: Clinical Laboratory Techniques for the 1980's* at pp. 393-410, R. M. Nakamura, W. R. Dito, and E. S. Tucker III, editors, Alan R. Liss Inc., New York, N.Y. (1980)

Previous techniques to detect and assess activation of the alternative complement pathway have generally been of two types. The first type involves demonstration of reduced functional activity of components of the alternative pathway such as C3 and factor B, in human sera after blocking the classical pathway. See for example, Perrin et al., *J. Exp. Med.*, 143:1027-1041 (1976); Ferrone et al., *Proc. Natl. Acad. Sci. USA.*, 70: 3665-3668 (1973). A variant of this method is to assess the deposition of components of the alternative complement pathway in diseased tissue. See Verroust et al., *J. Clin. Invest.*, 53:77-84 (1974). Such methods suffer from the following limitations: , (a) the alternative complement pathway activation is not directly measured, rather only the secondary consequences of activation, (b) multiple purified complement components must be prepared in the testing laboratory which must also possess facilities that verify functional activity, and, (c) the method does not permit quantification.

The second type of method used to measure activation of the alternative pathway detects the deposition of components of the alternative pathway such as C3 or factors B and H on the surface of the activator particle. See Schreiber et al., *Proc. Natl. Acad. Sci. USA.*, 75:3948-3952 (1978). A variant of this procedure is to measure the specific ratios of these components such as the factor H to C3 ratio. See Pangburn et al., J. Immunol, 124:977-982 (1980).

While activation is directly assessed in the above procedure and can be quantified, there are certain limitations. These limitations include (a) the requirement to purify and radiolabel multiple complement components in the testing laboratory and the associated requirement for facilities to verify functional integrity, (b) the involved techniques and interpretation of results are complex and require intimate familiarity with the system and, (c) the approach cannot be used to detect and quantify preexisting activation, and thus cannot be used with sera or plasma samples from patients.

Other attempts have been directed to the detection and measurement of inactivated products such as C1 inactivator bound to subcomponents of C1. See Harpel et al. *Clin. Res.*, 30: 563A (1982) and Hack et al., *J. Immun.*, 127: 1459 (1981). However, these systems are not directed to activated complexes which continue complement activity. Rather they are relative "dead end" products whose presence is not necessary indicative of the amount of complement pathway activation. The detection of these products was performed because they are known to be relatively stable and therefore available for assay. However, such products can remain as residuals in the blood and can be formed when there is no further activation of a complement system.

Further background information on the operation and measurement of the complement system can be found in Cooper, "The Complement System" in *Basic and Clinical Immunology*, pp. 124-135, Stites et al. editors, Lange Medical Publications, Los Altos, Calif. (1982); H. Rapp and T. Borsos, *Molecular Basis of Complement Action*, pp. 81-83, Appleton-Century Crofts, New York, N.Y. (1970); Muller-Eberhard, et al., *Adv. Immunol.*, 29:1-53 (1980); Pangburn et al., *J. Immunol.*, 124:977-982 (1980); Schreiber et al., *Clin. Immunol. and Immunopathol.*, 15:384-396 (1980); Platts-Mills et al., *J. Immunol.*, 113:348-357 (1974); Lesavre et al., *J. Immunol.*, 123:529-534 (1979); Polhill et al., *J. Immunol.*, 121:363-370 (1978); Fearon et al., *J. Immunol.*, 115:1357-1361 (1975); Day et al., *Scand. J. Immunol.*, 5:715-720 (1976); Chapitis et al., *J. Exp. Med.*, 143:241-257 (1976).

It would be desirable to provide a method and system which avoids the difficulties of the prior art procedures and provides for effective detection and quantification of activation of the complement system. Such detection of activation would be directed not to a whole sequence or a regulator protein, but to an activated complex which is indicative of the dynamic activity of a pathway. It would also be desirable if such a system and method were relatively easy to use and highly specific to the complement complex being assayed. The system and method should also be sensitive and able to detect relatively small amounts of complement activation. The present invention meets these desires.

SUMMARY OF THE INVENTION

The present invention is directed to an assay method and system which allow for the detection, and preferably also quantification, of an activated complex whose presence is indicative of complement system activation. The activated complex can be any of the complexes which form during the cascade of complement pathway activation and continue the activity of that pathway. Such a complex is an intermediary which continues complement activity by cleaving or binding with other components or assisting in cell lysis. This is distinguished from complexes which are inactivated or inhibited and, accordingly are not indicative of the extent and activity of pathway activation. It has been unexpectedly found that such an activated complex, despite being part of a cascade, can still be detected and measured as an accurate means of indicating complement pathway activation.

The activated complex comprises a first complement component and a second complement component. These components should not be confused with the complement components C1 and C2. Rather the first and second complement components can be separately chosen from any of the complement components, provided that the resulting complex is an activated complex. At least two binding agents specific to the components in the activated complex are used in the assay process of this invention.

In the assay method of this invention, a liquid sample such as serum is assayed by binding a first specific binding agent to any first complement component which may be present in the sample, including any first complement component in the complex. This can be done by contacting the first specific binding agent with the sample. The first specific binding agent is preferably an antibody to the first complement component, but can also be any specific binding agent such as the Fab or Fab' or F(ab')$_2$ portion of such an antibody, or the idiotypic region of the antibody provided it remains functional and still capable of binding. The use of the entire antibody is preferred over the use of lower molecular weight fractions since a whole antibody is easier to obtain. The first specific binding agent is preferably purified prior to use by well known affinity methods to substantially remove materials that do not bind with the first complement component.

A second specific binding agent is bound to any second complement component present including any second complement component forming an activated complex with the first complement component. The first and second specific binding agents bind to the complex to form an aggregate. The second specific binding agent includes a label used to identify and quantify the presence of the complex. The label can be of any suitable form such as an enzyme, a fluorochrome dye, or a radioactive nuclide. Enzyme and radionuclide labels allow for particularly sensitive measurement, and thus are preferred. The second specific binding agent, like the first, is preferably affinity purified and a whole antibody, but can also be an antibody fragment which includes the functional idiotypic portion of the antibody. The label can be linked to the antibody by known means.

The specific binding agents can be provided in kit form to form a diagnostic assay system. The specific binding agents need not be bound to the complex in any specific order, and can even be bound substantially simultaneously, that is, added to the sample at the same time if desired. However, it is preferred to bind the first specific binding agent to any activated complex present, remove the remainder of the sample and then bind the second, label-including, specific binding agent. Second specific binding agent is thus not wasted on second complement component not part of the activated complex.

After the aggregate is formed, any second specific binding agent including its label, not bound to the complex and part of the aggregate is preferably removed by an appropriate separation process. It is then possible to determine the presence, and preferably measure the amount of label which remains bound to the complex as part of the aggregate.

The separation process can be accomplished by many means. Since the aggregate comprising the complex bound with the first and second specific binding agents has a greater molecular weight than the labelled second specific binding agent alone or bound to any free second complement component, separation can be made by a molecular weight-size selective process. Such techniques include gel diffusion, chromatography, absorption, electrophoresis, centrifugation, and ultrafiltration. Separation can be further enhanced by coupling the first specific binding agent to a separation means such as an insoluble bead carrier.

A preferred separation means is a solid matrix or support on which the first specific binding agent is immobilized. Any excess sample portion which does not bind with the first specific binding agent can then be washed away with an aqueous solution of mild detergent leaving the activated complex immobilized. The second specific binding agent can then be contacted with the activated complex to form the aggregate. The aggregate formed is also immobilized allowing unbound second specific binding agent together with its label to be easily washed away before measurements are made. A particularly suitable solid matrix is a multiple well microtitration plate commonly used in immunochemistry. Such a plate can be provided as part of an assay kit with the first specific binding agent pre-bound or in solution to be immobilized before use.

The first specific binding agent can be immobilized on the microtitration plate and stored until ready for use. Such a prepared microtitration plate can be provided as part of an assay system to perform the method of the present invention. The microtitration plate preferably has two groups of wells, a group of sample wells in which predetermined volumes of sample are placed and a group of standard wells retaining various known amounts of second complement component. Second specific binding agent also forming part of the assay system can be added to all the wells. After unbound label is removed, measurements of the sample wells can be compared to the standard wells as a reference.

The complex being detected can be any one of several activated complexes which are formed when the complement system is activated. These include the $\overline{C4b,2a}$ and $\overline{C4b,2a,3b}$ complexes which are formed when the classical pathway is activated. Also useful are the $\overline{C3b,Bb}$, $C3b_nBb$ and $\overline{C3b_n,P,Bb}$ as well as the particularly preferred complexes comprising C3b and properdin (P) which are present in sera when the alternative pathway is activated. The presence of the activated complexes that are combinations of C5b and C6–C9 and are formed along the common terminus of both the classical and alternative pathway may also be detected. Complexes which are inactivated or inhibited by one of the regulator proteins are not of interest since they are relative "dead ends" which are not indicative of the amount of activation.

Depending on the complex being assayed for, the specific binding agents are preferably antibodies to two of the following: C2a, C3b, C4b, Bb, properdin, C5b, C6, C7, C8, and C9. In one particularly preferred embodiment, an activated complex including C3b and properdin (P) is detected in serum. In this embodiment, the first specific binding agent includes a first anti-P antibody and the second specific binding agent includes a second anti-C3b antibody.

Because the specific binding agents, antibodies, are directed to two different components in the complex and the complex is "sandwiched" in between the two binding agents to form the aggregate, the assay is not only very specific, but is also particularly sensitive. For example, a properdin- and C3-containing complex is only formed as a result of alternative pathway activation. Properdin is naturally present in serum even without alternative pathway activation and can bind with the anti-properdin antibody. However, such binding will not produce a false positive result. Since the label is linked to the anti-C3 antibody, detection and measurement only occurs when the anti-C3 antibody binds to the C3b forming part of a complex which is bound to the anti-properdin antibody. Any anti-C3b antibody not bound to the complex or bound to C3b which is not part of the complex is, together with its linked label, separated from the aggregate. This is not only highly specific, but is also sensitive and able to reproducibly detect 10–20 nanograms per milliliter (ng/ml) of complex in serum. Where the complex being detected comprises C3b and P, this value corresponds to 0.0015 percent of the C3 normally present in serum. The stability of the complexes in sera or plasma allows stored sera and samples collected under non-optimal conditions to be assayed.

The present invention differs from other so-called "sandwich" assays known in the art. In the present invention, a pre-existing activated complex having at least two molecular components is sandwiched between two specific binding agents. In one of the more usual "sandwich-type" assays, an antigen and antibody form a complex in situ during the assay and a second antibody raised to the first antibody is utilized as the third component of the assay. In another usual type of "sandwich" assay, one antigenic protein having two determinant regions is bound using an antibody to each of the determinant regions. Neither of those more usual assays utilizes a preformed bimolecular complex as the inner portion of the sandwich.

The present invention has considerable advantages over previous methods because it detects and can measure the amount of a particular activated complex that is only present in serum as a result of complement activation. For example, the measurement of erythrocyte lysis in a hemolytic assay measures the residual functional activity of the complement components and not the amount of activation. Hemolytic assay is also dependent on a secondary event, the lysis of the cell membrane, which in turn is dependent on the integrity of the membrane attack pathway. Thus, hemolytic assay is not effective in detecting complement pathway activation in a patient having a deficiency in one of the C5 through C9 components. Such deficiency can be associated with gonococcal septicemia, disseminated lupus erythematosus and recurrent or isolated meningococcal meningitis. Such deficiencies do not represent a problem with the present invention except in the rare situation that the deficient complement component is one of those utilized in the assay.

Numerous other advantages and features of the present invention will become readily apparent from the following detailed description of the invention, the drawings, and the appended claims.

List of Abbreviations

ARDS=Adult Respiratory Distress Syndrome
BSA=Bovine serum albumin
Bb=Proteolytic fragment of complement Factor B
C1–C9=Components of complement
C3b=Major cleavage fragment of C3
CNBr=Cyanogen bromide
$E_R$=Rabbit erythrocyte
$E_S$=Sheep erythrocyte
EA=Erythrocyte amboceptor
EC3b=Erythrocytes with bound C3b
EDTA=Ethylenediaminetetraacetic acid
EDTA-NHS=Normal serum containing 20 millimolar EDTA
EGTA=Ethylene-bis-(oxyethylenenitrilo)tetraacetic acid
ELISA=Enzyme linked immunosorbent assay
H=Co-factor of factor I
I=Inactivator of C3
MgEGTA-NHS=Normal human serum containing 2.5 millimolar magnesium and 10 millimolar EGTA
NHS=Normal human serum
P=Properdin
PAP=Purified alternative pathway proteins
PBS=0.012M Phosphate buffer in 0.15 molar NaCl
R.I.=Restriction index defined as the ratio of H molecules bound to C3 molecules bound to an activator particle
SLE=Systemic lupus erythematosus
VBS=Veronal Buffered Saline
VBS++=Veronal Buffered Saline with $Ca^{+2}$ and $Mg^{+2}$

BRIEF DESCRIPTION OF THE DRAWINGS

In the drawings forming a portion of this disclosure.

DESCRIPTION OF THE INVENTION

I. Introduction

Figure 1:
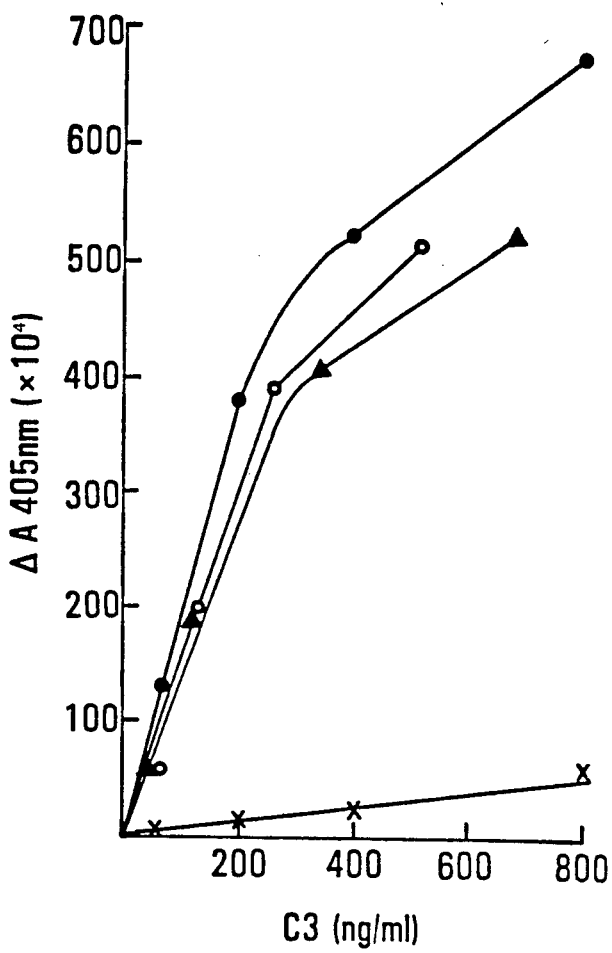
FIG. 1 is a graph illustrating ELISA determinations of C3 preparations that were used as standard references. Three different preparations of purified human C3 designated by dots, circles and triangles were diluted from 50 to 800 nonograms per milliliter and placed into wells that had been precoated with anti-C3. C3 was dessicated in uncoated wells designated by X's. After washing, enzyme-labeled immunospecific anti-C3 was added followed by enzyme substrate. Optical absorption caused by enzyme-substrate reaction was measured and plotted.

The present invention is directed to an assay method and system for detecting and measuring an activated complex of the complement system in a sample. The sample can be body fluid taken from a patient or from a synthetic complement system useful in the study of how various infective agents affect the complement system. The preferred body fluid for assay is serum, but other body fluids which can also be used include plasma, blood, synovial fluid, cerebrospinal fluid, fluid within bullae, pleural and pericardial effusions, urine and saliva. The presence of the activated complex in a body fluid is indicative of complement pathway activation. For ease of description, the use of sera will be described as illustrative of such body fluids.

The activated complement complex is present in sera only when the complement system has been activated. The activated complex continues the activity of the complement system by coacting with other complement components or by assisting in cell lysis. This complex includes a first complement component and a second complement component. Additional complement components can also be present in the complex. Such activated complexes include $\overline{C4b,2a}$; $\overline{C4b,2a,3b}$; $\overline{C3b,Bb}$; $\overline{C3b_n}$, $\overline{Bb}$; $\overline{C3b_n,P,Bb}$; $\overline{C3b,P,Bb}$; $\overline{C3b_n,P}$; complexes having C3b and properdin, and C5b in combination with one or more of the following: C6, C7, C8, and C9.

In the assay aspect of this invention, a sample believed to contain an activated complement complex can be tested to determine the presence of and preferably measure the amount of such complex. A first specific binding agent is bound to any first complement component present in the sample including any first complement component forming part of the activated complex. Such binding is usually accomplished by contacting the first specific binding agent with the sample. A second specific binding agent which includes a label is bound to any second complement component which may be present in the sample including any second complement component forming part of the complex. The binding of the first and second specific binding agents to the complex forms in an aggregate. The binding agents need not be bound to the complex in any particular order and can even be introduced together into the sample to be bound at about the same time.

After the aggregate has been formed, any second specific binding agent and hence its included label not forming part of the aggregate can be separated from the aggregate. The presence and preferably the amount of any label bound or linked to the complex and therefore performing part of the aggregate may then be determined.

There are several methods which can be used to separate the aggregate from second specific binding agent not part of the aggregate. Such agent may be unbound or bound to second complement component which is not part of an activated complex. Several methods utilize molecular weight-size selective processes in that the aggregate has a substantially greater molecular weight and size than the second specific binding agent which is not part of the aggregate. These methods include gel diffusion, chromatography, adsorption, electrophoresis, centrifugation, ultrafiltration and fractional precipitation. Some of these methods also rely to a certain extent on the chemical and electrical properties of unbound second specific binding agent and aggregate.

To further enhance separation and removal of the aggregate from the second specific binding agent not forming part of the aggregate, the first specific binding agent present can be pretreated, e.g. by coupling to a separation means. The separation means can increase the mass of the aggregate or change its electrical properties to enhance separation. A mass increase can be accomplished by using a carrier as the separation means. Such carriers include relatively large, polymeric molecules such as water-soluble hydroxyethyl cellulose and hydroxypropyl cellulose derivatives, polyethyleneimine, polylysine, polyglutamic acid and proteins such as keyhole limpet hemocyanin or ferritin (M.W. 460,000), or natural or synthetic polymeric magnetic materials such as iron-cross-linked acrylic or methacrylic acid containing polymer to which a specific binding agent may be linked. Even larger physical objects such as insoluble particles or beads of glass, the dextran available under the trademark SEPHADEX from Pharmacia Fine Chemicals, Piscataway, N.J., agarose, polystyrene, or acrylamide can also be used as carriers. With such insoluble particles, simple centrifugation can be used without the need of an ultracentrifuge. There need not be complete separation as into two containers, but partial separation as with the aggregate and separation means sinking or precipitating to the bottom of a container while the unbound label remains for the most part in the upper portion of the container is acceptable.

It is preferred that the separation means be a solid material such as a solid matrix or support on which the first specific binding agent is immobilized. Such a solid matrix can be the surface of microtitration plates having a plurality of wells as are commonly used for immunochemistry. Such plates containing ninety-six wells each are commercially available under the trademark IMMULON II from Dynatech Laboratories, Alexandria, Va. The solid matrix should then be treated to prevent binding with the second specific binding agent. A solution of bovine serum albumin (BSA) is suitable for use with plastics.

Where the first specific binding agent is a first antibody, *Staphylococcus aureus* protein A can . be used to bind the Fc region of the first antibody to a matrix and immobolize it. *Staphylococcus aureus* protein A can also be used as a carrier or as part of the first specific binding agent to give it a "sticky tail" which will attach to a plastic matrix. A still further technique is to include as part of the first specific binding agent the vitamin biotin. Proteins such as antibodies can be biotinylated as discussed by Berger et al., *Molecular Immunology*, 19: 857-864 (1982). The extremely high affinity of avidin, a protein from egg white, for biotin (association constant $10^{15}$) allows for easy separation as through precipitation.

After the aggregate has been formed and immobilized on the solid matrix by the first specific binding agent, any unbound second specific binding agent and label can be easily washed away. Suitable for washing is a dilute nonionic detergent solution containing detergents such as those commercially available under the trademarks TWEEN 20 or TWEEN 80 by ICI Americas, Inc., Wilmington, Del., or TRITON X-100 available from Rohm & Haas Co., Inc. of Philadelphia, Pa. After washing, the presence and amount of label remaining as part of the aggregate can be easily measured.

While it is preferred to separate any second specific binding agent and hence its label which does not form part of aggregate, from the aggregate, such a separation is not always necessary. Separation is not needed when the first specific binding agent affects the operation of the label included as part of the second specific binding agent. One example of this would be fluorescent quenching.

Another example is where the first specific binding agent includes a chemiluminescent catalyst such a peroxidase or luciferase which when reacted with their respective substrates emit light through a chemical reaction. Alternatively, the first specific binding agent can include a light absorbing compound such as carboxylated benzophenone which absorbs ultraviolet light and can transfer the absorbed energy through an excited state to another molecule. The label on the second specific binding agent is then a fluorescent molecule such as porphyrin or an aromatic compound. Light is then absorbed and re-emitted or produced by the first binding agent at a first wave length, and absorbed and readmitted by the fluorescent molecule with the second binding agent at a second wave length. It is the presence of light at this second wave length which is indicative of the presence and amount of aggregate and therefore activated complement complex in the sample.

It is preferred that the specific binding agents be antibodies to their respective complement components. Other suitable specific binding agents include parts of the appropriate antibodies such as the Fab, Fab' or F(ab')$_2$ regions and the functional idiotypic regions, all of which can be referred to as functional idiotype-containing polypeptides. The idiotype-containing polypeptide is functional in that its idiotypic region binds to the same determinant domain as does its corresponding intact antibody. Inasmuch as antibodies are discussed as being "raised" to antigens, functional idiotype-containing polypeptides may also be discussed as being "raised" to antigens. The whole antibody is the preferred functional idiotype-containing polypeptide since it is more readily available. For ease of explanation, antibodies will be used illustratively as representative of functional idiotype-containing polypeptides. The first specific binding agent can thus be a first antibody and the second specific binding agent can be a second antibody. The antibodies can be from a monoclonal source if desired.

Each specific binding agent can include more than one antibody or functional idiotype-containing polypeptide. For example, the second specific binding agent can include an unlabeled second antibody and a third antibody to the Fc region of the second antibody. The label can then be linked to the third antibody. The third antibody can be bound to second antibody prior to contact with the complex, or can be bound seriatim after the second antibody has bound with the complex. In the later case, where the complex has already been bound or immobilized with a first antibody, the first and second antibodies must be selected from different animal species to avoid the binding of the third antibody directly to the first antibody.

The label can be any suitable label which allows for identification and quantification. Such labels include enzymes, and tracers which can either be fluorochrome dyes or radioactive isotopes such as iodine 125 or 131, hydrogen 3 and sulfur 35. Suitable fluorochrome dyes which can be linked to the second specific binding agent for labeling by immunoflorescence include beta-anthracene, rhodamine and fluorescein. Radioimmunoassay and enzyme immunoassay are particularly advantageous because of their relatively high sensitivity. Enzyme immunoassay has advantages over radioimmunoassay in that radioactive materials with relatively short half lives need not be handled and stored.

The enzyme chosen should be relatively stable, have a relatively long shelf life, be readily available and inexpensive. The activity of the enzyme should also be easily measurable using simple colorimetric or fluorometric methods with small amounts of enzyme being detectable. Therefore, the enzyme should have a high substrate turnover number and not be affected by biological components in the test sample. Such enzymes include alkaline phosphatase, horseradish peroxidase, glucose oxidase, catalase, and beta-D-galactosidase. For a discussion of such enzymes and substrates, see generally, Maggio, *Enzyme-Immunoassay*, CRC Press, Boca Raton, Fla. (1980).

In the case where an antibody serving as a binding agent is immobilized, e.g. by being coupled to a microtitration plate, and an enzyme is used as a label, the assay method is of the general type known as Enzyme-Linked Immunosorbent Assay (ELISA).

The enzyme can be linked to the second antibody by either a one-step conjugation method where the two components are mixed together with a cross-linking agent such as glutaraldehyde, or in a two-step procedure. In the two-step procedure, either the antibody or the enzyme is reacted alone with the linking agent and after removal of excess linking agent, the resultant activated product is mixed with the other desired component. In the one-step method, each component cross-links with itself as well as with the other, whereas in a two-step method, only the first component will be self-linked. Gel filtration may then be employed to remove unlabeled antibody.

Alkaline phosphatase, upon reaction with its substrate, p-nitrophenyl phosphate, a chromogen, produces a generally yellow appearance having a maximum absorbance at about 405 nanometers (nm) (24,700 cm$^{-1}$) The change in optical density per unit time can be measured to provide both an accurate and highly sensitive measurement of the amount of enzyme and, therefore, enzyme-bound aggregate present. It is preferred that standard, control wells also be utilized to provide a standard curve for comparison and conversion from change in optical density to milligrams of material present. This is discussed in more detail below.

A preferred and illustrative embodiment of the present invention assays for activation of the alternative complement pathway, and in particular measures the amount of a complex present which includes C3b and properdin. Such a measurement is useful in the identification of certain diseases and pathological conditions as discussed above.

In the assays discussed in more detail below, the following procedure was generally followed. Most of the rows (sample wells) in a ninety-six well microtitration plates were coated with five micrograms/milliliter of affinity purified anti-properdin antibody as the first antibody and allowed to dry overnight. Replicate samples of purified C3 (5 to 40 micrograms) for the purpose of generating a standard reference curve were placed in the remaining rows (standard wells) to provide a C3 standard. All of the wells in the plate were treated with a solution of 0.5 percent bovine serum albumin (BSA) in phosphate buffered saline (PBS) for two hours at 37 degrees C. to block the walls of the wells from binding to subsequently introduced proteins such as the second or anti-C3 antibody. The plate was then aspirated and washed once in a solution of PBS-TWEEN 20.

Replicate serum samples were added to the coated and blocked sample wells and allowed to bind for one hour at room temperature. Serum samples were not added to the standard rows containing purified C3. The sample wells were then washed three times in a solution of PBS-TWEEN 20. Affinity purified anti-C3 antibodies conjugated to alkaline phosphatase were then added to all of the wells and allowed to bind one hour at room temperature. The wells were again washed three times in a solution of PBS-TWEEN 20.

Thereafter, known amounts p-nitrophenyl phosphate were added as chromogens and the plates were read at 405 nm at five minute intervals in an automated microtiter reader. The change in optical density at 405 nm was calculated for the assay samples and the C3 standards. By comparison with the C3 curve obtained in the same experiment, the amount of C3, and therefore the amount of properdin-C3b complex detected in the experimental samples, were expressable in nanograms/well. These values may then be converted to nanograms/milliliter by knowledge of the amount of sample placed in each well.

While anti-C3 antibody was used, it should be kept in mind that an anti-C3b antibody is also an anti-C3 antibody. The majority, about ninety five percent, of C3 is the C3b moiety. Accordingly, for practical purposes anti-C3 antibody is also anti-C3b antibody.

Other possible variations include: using functional anti-properdin and anti-C3b idiotype-containing polypeptides, binding the anti-C3b antibody to the solid matrix with the label linked to the anti-properdin antibody, or the use of anti-Bb antibody in conjunction with either anti-properdin or anti-C3b antibody to measure the presence of $\overline{C3b,P,Bb}$ and $\overline{C3b,Bb}$ complexes. Alternatively, activation of the classical pathway can be determined by choosing antibodies to two of the following: C2a, C3b, and C4b. Activation of the common terminal trunk of the complement pathway can also be measured by choosing antibodies to two of the following: C5b, C6, C7, C8, and C9.

The assay method for determining activation of the complement system can be practiced through use of a diagnostic assay system containing the necessary materials in kit form. Generally, such a system comprises the first specific binding agent and the second specific binding agent which includes the label. Where the label is an enzyme, an enzyme substrate can also be provided. In the kit, the several specific binding agents and enzyme substrate are preferably packaged separately.

The first specific binding agent can be provided in solution to be immobilized on a solid matrix before use or can be coupled to a separation means such as a carrier as discussed above. The second, labeled, specific binding agent and its substrate, if needed, can also be provided in one or more solutions as are necessary to simplify use. While an antibody dispersed in a liquid may not be a true solution in the strict sense of the word, for purposes of this discussion, it will be considered as a solution.

Figure 11:
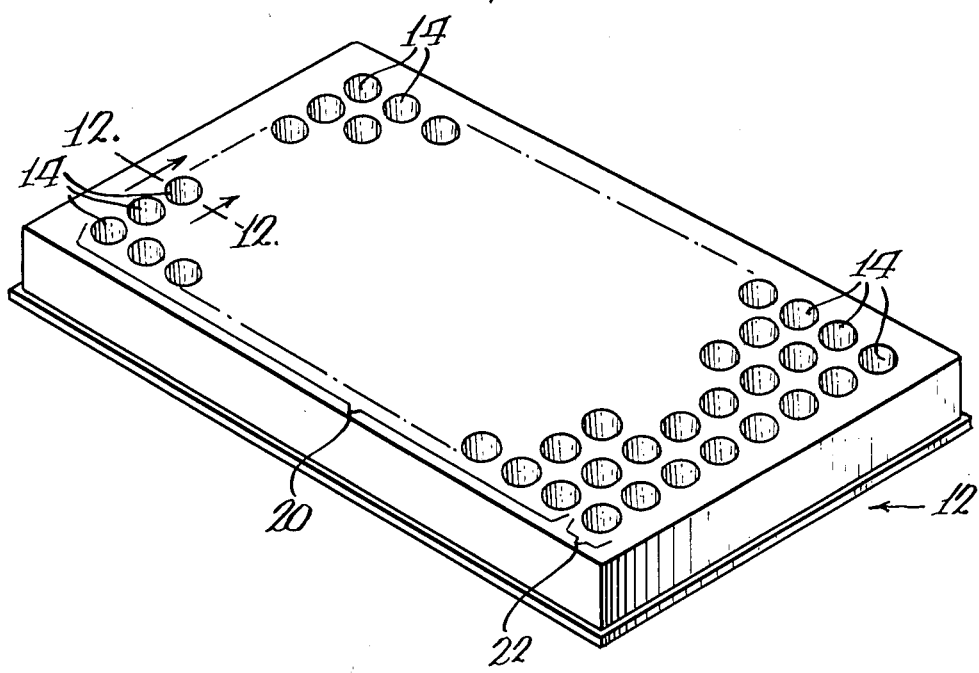
FIG. 11 is a perspective view of a microtitration plate having a plurality of wells.
Figure 12:
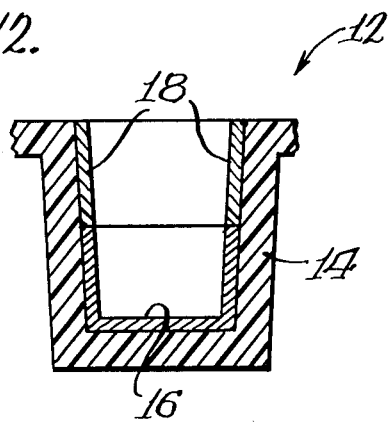
FIG. 12 is an enlarged cross-sectional elevational view of one of the wells in the plate of FIG. 11 taken generally along plane 12-12.

For ease of use, the first specific binding agent is provided coupled and immobilized on a solid matrix or support such as a microtitration plate 12 having a plurality of wells 14 as shown in FIG. 11. An optimal arrangement includes the specific binding agent 16 immobilized on the lower or bottom portion of the wells 14 as shown in FIG. 12. A blocking protein 18 such as BSA is shown as occupying the upper portion of the wells 14.

The microtitration plate 12 is preferably made of any suitable material that is clear and adsorbs or permits linking of the first specific binding agent so that the binding agent is retained in the wells even during washing. Such materials include polystyrene, polyvinyl chloride, polypropylene, polycarbonate or treated glass. The wells preferably have flat bottoms to provide an appropriate optical surface through which the amount of label may be read spectrophotometrically.

The plate 12 is preferably divided into two sections, a sample section 20 having a plurality of sample wells in which the samples to be assayed are placed, and a standard section or row 22 having a plurality of standard wells in which standard, control, samples have been or will be placed. The wells in the sample section 20 are provided with first specific binding agent 16 present in an amount in excess of the expected amount of first complement component in the samples to be assayed. The wells in the standard section 22 retain varying known quantities of second complement component. The second complement component can be retained in the well by being coupled to an immobilized second specific binding agent in the well. Alternatively, standard second complement component solution can be provided to be added to otherwise empty wells of standard section 22.

II. Materials and Methods
Reagents and Buffers

TWEEN 20, fraction V bovine serum albumin, p-nitrophenyl phosphate, type VII alkaline phosphatase from calf mucosa (Sigma Co., St. Louis, Mo.), diethanolamine (Eastman-Kodak Co., Rochester, N.Y.), neuramininidase (Gibco Laboratories, Grand Island, N.Y.), tetanus toxoid (Lederle Laboratories, Pearl River, N.Y.), heparin, as Lipo-Hepin U.S.P. units/milliliter, Riker Laboratories, Riker Laboratories, Northridge, Calif.) and calf thymus DNA (Worthington Laboratories, Freehold, N.J.), were purchased from the referenced manufacturers. VBS and VBS++ with calcium and magnesium were prepared as described by Mayer in *Experimental Immunochemistry* at p. 133 (1967). PBS contained 12 millimolar phosphate and 150 millimolar NaCl, pH 7.4.

Human Sera

Venous blood from normal individuals was clotted in glass tubes for one hour at room temperature, centrifuged and the sera removed and stored at −70 degrees C. Sera from patients diagnosed to have ARDS were generous gift of Dr. Charles Cochrane of the Research Institute of Scripps Clinic. Sera from patients diagnosed to have typhoid fever were obtained from the U.S. Naval Medical Research Unit No. 2, Jakarta Detachment. Sera from patients with systemic lupus erythematosis were kindly supplied by Dr. John Curd of Scripps Clinic and Research Foundation.

Complement Deficient And Depleted Sera:

C2-deficient and C7-deficient human sera were from individuals with a genetic deficiency of the respective proteins. C2-, C3-, B- and C4-depleted sera were made by passing serum samples through affinity columns bearing the IgG fraction of the appropriate monospecific antisera in 10 millimolar (mM) EDTA. Absence of the appropriate component was determined by Ouchterlony analyses and specific functional assays. Only sera which could be substantially reconstituted at least 80 percent in functional activity by the addition of physiological levels of the missing protein in purified form (together with Clq) were used.

Complement Pathway Proteins and Cellular Intermediates:

C3 was purified to homogeneity from human serum as described by Tack et al., *Biochemistry*, 15:4513–4521 (1976). Factor B was purified to homogeneity from human serum as described by Gotze et al., *J. Exp. Med.*, 134:905–1085 (1971). Factor D was similarly prepared as described by Gotze et al., *J. Exp. Med.*, 139:44–57 (1974), and Factors H and I were similarly prepared as described by Pangburn et al., *J. Exp. Med.*, 146:257–270 (1977).

C3b was prepared as described by Pangburn et al., *J. Exp. Med.*, 146:257–270 (1977). C3b dimers, C3bi, C3c and C3d were prepared as described by Schreiber et al., *Clin. Immunol. and Immunopath.*, 23:335–357 (1982). Clq and nephritic factor were prepared as described by Tenner, et al., *J. Immunol.*, 127:648–653 (1981), and Schreiber et al., *J. Exp. Med.* 142:760–772. (1979)

Properdin (P) was purified by a modification of the method of Medicus et al., *J. Immunol.* 124:602–606 (1980). EDTA was added to normal serum to a concentration of 5 millimolar and the serum was passed over BioRex 70 (Trademark of BioRad Laboratories, Richmond, Calif.), as previously described for Clq purification by Tenner et al., above. Fall thru fractions containing properdin were pooled and dialyzed into 20 millimolar Tris-HCl containing 30 millimolar NaCl, pH 8.5, K=3.9. The remainder of the procedure was as published by Medicus et al. Activated properdin was generated by repetitive freeze-thawing of the preparation. C3 was radiolabeled with $^{125}$I by the lactoperoxidase procedure (Enzymo beads, a trademark of BioRad Laboratories of Richmond, Calif.) to a level of 1 microcurie/gram and used within a week of radiolabeling.

Mixtures of the purified alternative pathway components C3, B, D, H, I, and P at physiological concentrations (PAP) were prepared in VBS and used as described by Schreiber et al., *Proc. Natl. Acad. Sci., USA*, 75:3948 (1978). Sheep erythrocytes ($E_s$) bearing only C3b were generated with purified C3 and Factors B, D, and nephritic factor as described by Pangburn et al., *Proc. Natl. Acad. Sci., USA*, 75:2416 (1978). The cells carried about 50–100,000 C3b molecules on their surfaces.

Activator And Non-Activator Particles:

Sheep erythrocytes ($E_s$), were purchased from Colorado Serum Company (Denver, Colo.), and rabbit erythrocytes, ($E_R$), were obtained from normal laboratory rabbits washed 3 times in VBS++ and resuspended at various concentrations in the same buffer for use.

Raji cells from a Burkitt's lymphoma cell line were grown in RPMI 1640 supplemented with 10 percent fetal calf serum (Rehatuin, Kankakee, Ill.), 2 millimolar glutamine (Gibco, Grand Island, N.Y.), penicillin and streptomycin. The cells were harvested at a concentration of $1 \times 10^6$/milliliter, washed two times in PBS and viability ascertained to be at least 95 percent by trypan blue exclusion before use.

Gram negative bacteria included serum sensitive *E. coli* 04 and serum resistant *K. pneumonia* laboratory strains. The bacteria were grown in trypticase soy broth (Becton-Dixon Co., Cockeyville, Md.) and harvested at a concentration of $1 \times 10^9$/milliliter, as determined by nephelometry and colony forming unit determination. The organisms were washed three times in VBS$^{++}$ and heat killed for 1 hour at 80 degrees C. before use.

Zymosan A (Sigma) was boiled for 2 hours in 0.15 molar NaCl. The particles were washed in VBS++ and resuspended to approximately 50 milligrams/milliliter and frozen at −70 degrees C. in aliquots until use.

Human tetanus-anti-tetanus immune complexes were generated as described by Ziccardi, *J. Immunol.*, 128:2505 (1982). The final suspension contained 1–2 milligrams/milliliter of protein by Folin-Lowry determination. See generally Lowry et al., *J. Biol. Chem.*, 193:265 (1981).

Epstein-Barr virus was prepared as described by Nemerow et al., *J. Immunol.*, 127:272-278 (1981), influenza WS/33 virus was prepared as described by Beebe et al., *J. Immunol.* 130, 1317-1322 (1983) and Moloney Leukemia virus prepared as described by Cooper et al., "*J. Exp. Med*"., 144:970-984 (1976).

Affinity Purification of Anti-C3 And Anti-Properdin For Use In The ELISA:

Ten milligrams of C3 and 1 milligram of properdin were separately coupled to 1 gram of CNBr activated SEPHAROSE 4B (Pharmacia, Piscataway, N.J.) using the instructions of the manufacturer. Monospecific goat anti-C3 and rabbit anti-P sera were precipitated with 33 percent ammonium sulfate. The precipitates, after dissolution and dialysis into VBS, were passed through the appropriate C3 or properdin columns in VBS. After extensive washing with 3 molar NaCl in VBS, the columns were stripped with 0.2 molar glycine-HCl, pH 2.2 as discussed by Nakamura in *Immunopatholoqy Clinical Laboratory Concepts and Methods*, Little, Brown and Company, Boston, Mass., p.659 (1974). The protein-containing fractions were pooled, immediately neutralized, and dialyzed into PBS. The affinity purified antibodies were frozen at $-70$ degrees C. until use.

Alkaline Phosphatase Labelling of Antibodies:

Alkaline phosphatase (Sigma, type VII) was conjugated to the above described affinity purified anti-C3 by the method described by Voller et al. in *Manual of Clinical Immunology*, N.R. Rose, H. Friedman, ed., published by the American Society for Microbiology, Washington D.C., p.p. 359-371 (1980). The dilution of the enzyme labeled antibody to C3 to be used was determined by adding 1:100 to 1:5000 dilutions to wells of microtitration plate (Linbro STERILE/TITERTEK, a trademark of Linbro Laboratories, Manden, Conn.) previously coated with affinity purified IgG antibody to C3 (5 micrograms/milliliter) followed by a 1:10,000 dilution of serum (see below). The ELISA was then performed as described below and the highest conjugate dilution giving an optical density reading of just under 2.0 at 405 nanometers determined. This dilution was generally about 1:750.

C3 Standard Curve And Conversion Of Elisa Values To Nonograms of C3b:

A standard curve was generated in each determination. Two fold dilutions of purified human C3 (1 to 300 nanograms/milliliter) in 0.1 milliliter volumes in VBS were added in duplicate to standard wells that had been precoated with anti-C3. Precoating was accomplished by dessication in each standard well of 0.1 milliliter volumes of 5 micrograms/milliliter solution of anti-C3 in PBS overnight. Subsequent steps were exactly as described in the next section on the ELISA. A linear relationship between optical density at 405 nanometers and C3 concentration prevailed to a C3 concentration of 300-500 nanograms/milliliter.

Enzyme-Linked Differential Antibody Immunosorbent Assay:

The assay was a modification of the standard ELISA method described by Voller et al., above. The sample wells in microtitration plates were coated with 0.1 milliliter volumes of the affinity purified anti-properdin antibody at a concentration of 5 milligrams/milliliter in PBS by overnight dessication. Next, 0.2 milliliters of PBS containing 0.5 percent BSA were added to each sample well and the plates incubated for two hours at 37 degrees C. in a humid incubator. After removal of this blocking solution, the plates were washed once with PBS containing 0.05 percent TWEEN 20 (PBS-Tween).

Dilutions of samples to be tested for ELISA reactivity in PBS-Tween-10 millimolar EDTA-0.25 percent BSA (PBS-Tween-EDTA-BSA) were placed, in 0.1 milliliter volumes, in triplicate, into the coated sample wells. After rocking for 1 hour at room temperature, the plates were washed three times with PBS-Tween. Next, 0.1 milliliters of alkaline phosphatase conjugated to anti-C3 antibody diluted in PBS-Tween-EDTA-BSA were added to the sample and standard wells. The plates were again rocked for 1 hour at room temperature, and washed 3 times with PBS-Tween after which 0.1 milliliters of p-nitrophenyl phosphate at a concentration of 1 milligrams/milliliter in diethanolamine buffer, pH 8.9 was dispensed into the wells.

The plates were read at 405 nanometers after varying times (usually 10 to 60 minutes) in a TITERTEK Multiscan Photometer manufactured by Linbro Laboratories of Hamden, Conn. which was standardized to wells containing all reactants except the assayed samples. Since initial color development was linear with time, the optical density change per minute was calculated. Where appropriate, these values were converted to nanograms/milliliter of C3 by comparison with the standard curve. In all studies, another control included uncoated wells which received the reaction mixtures, conjugated antibody and substrate. Where appropriate, these values were subtracted from experimental wells.

General Procedure For Testing Samples For The Modified ELISA:

Normal human serum, normal human serum containing 2.5 millimolar $Mg^{+2}$ and 10 millimolar EGTA (MgEGTA-NHS) which were added to block participation of classical pathway components, complement component-deficient or complement-depleted sera or the PAP (in VBS) were incubated with an equal volume of a suspension of the activator in VBS. Generally, 50 microliter volumes were used. Unless otherwise specified $E_S$, $E_R$, neuraminidase treated $E_s$ and Raji cells were used at $1 \times 10^8$ milliliter; *E. coli* 04 and *K. pneumoniae* at $1 \times 10^9$/milliliter; zymosan at 2.5 milligrams/milliliter; human immune complexes at 2.0 milligrams/milliliter; heparin at 500 units/milliliter; DNA at 20 microgram milliliter; influenza virus at $1 \times 10^{10}$ particles/milliliter; Epstein-Barr virus at $1 \times 10^9$ particles/milliliter; and Moloney leukemia virus at 2 milligrams/milliliter protein.

The mixtures were incubated at 37 degrees C. and samples taken at intervals. When dose response rather than kinetic studies were carried out, equal volumes of MgEGTA-NHS and particles (from $1 \times 10^6$/milliliter to $1 \times 10^9$/milliliter) were incubated together for 40 minutes at 37 degrees C. The samples of the reaction mixtures were diluted in PBS-Tween-EDTA-BSA and triplicate 0.1 milliliter samples assayed. The dilution used for each activator was dependent on the potency or "strength" of the activator. For weak activators such as Raji cells bearing small amounts of P and C3b, dilutions of 1:10 to 1:20 were utilized, while for "strong" activators such as rabbit erythrocytes, higher dilutions such as 1:50 or 1:100 were used. Clinical sera were diluted 1:10 for assay.

Slight modifications were employed to assay the activation complex on the surface of the activator. These included washing after incubation of the activator with serum (in the case of erythrocytes) or centrifugation of 20 microliter aliquots of the reaction mixtures through a 300 microliter layer of 20 percent sucrose in PBS with 10 millimolar EDTA (in the case of bacteria or zymosan). The pellets were resuspended in smaller (i.e. 0.3–0.5 milliliters) or larger (i.e. 1.0–1.5 milliliters) volumes of PBS-Tween EDTA-BSA for weak or strong activators, respectively. Triplicate 0.1 milliliter samples were analyzed in the modified ELISA.

In some studies, supernatants of the activation mixtures were also tested. In these instances, samples of the reaction mixtures were diluted in PBS-Tween-EDTA-BSA and then centrifuged in the Beckman microfuge. Triplicate 0.1 milliliter samples of the supernatants were tested in the modified ELISA.

Binding of Properdin To C3b Coated Erythrocytes:

Equal volumes of increasing concentrations of activated properdin were incubated with erythrocytes having bound C3b (EC3b) ($2.5 \times 10^6$/milliliter in VBS$^{++}$) for 15 minutes at 37 degrees C. The cells were then washed, resuspended in VBS and triplicate 0.1 ml samples assayed in the ELISA.

Radiolabeled C3 Deposition On Activators:

MgEGTA-NHS to which radiolabeled C3 had been added was incubated at 37 degrees C. in equal volumes with suspensions of the activators. At intervals, 20 microliter samples were layered over 300 microliters of 20 percent sucrose solution in VBS containing 10 millimolar EDTA. After centrifugation for 5 minutes in a Beckman MICROFUGE (Trademark of Beckman Instruments, Inc., of Irvine, Calif.) the tips of the tubes were amputated and the pellets, supernates and remainder of the tube counted in a Packard AUTO-GAMMA Spectrometer (Trademark of Packard Instrument Co. of Downers Grove, Ill.). The radioactivity values were converted to molecules of C3 per activator particle by knowledge of the total C3 concentration of the radiolabeled C3 mixture (determined by Mancini analyses) and the specific radioactivity of the mixture. Duplicate samples of the same reaction mixtures were similarly centrifuged and the pellets analyzed in the ELISA as described above.

III. Assays

The C3 Standard Curve:

FIG. 1 shows the C3 ELISA standard curves in which known amounts of purified human C3 were diluted to 50–800 nanograms/milliliter and placed into wells which had been precoated with anti-C3 as described above. This was done for three preparations designated by the dots, circles and triangles. Alternatively, C3 from the same preparation represented by the triangles was desiccated in uncoated wells and represented by X's. After washing, enzyme-labeled immunospecific anti-C3 antibodies were added, and the ELISA was preformed as described above.

As shown in FIG. 1, the C3 standard curve yielded a linear relationship between the optical density and the C3 concentration to a level of about 300–500 manograms/milliliter. The lower limit of detection of C3 was 10 to 20 nanograms/milliliter (1 to 2 nanograms/well), a level which yielded an optical density of approximately 0.100 after one hour of incubation. The amount of C3 corresponds approximately to the amount in a $10^{-5}$ dilution of human serum (approximately 16 nanograms/milliliter). Different C3 preparations represented by the dots, circles and triangles yielded very similar standard curves.

In other studies (not shown) serum samples of known C3 content yielded substantially similar standard curves as purified C3. The repetitive standard curves, which were included in each assay and encompassed several preparations of affinity purified anti-P and enzyme conjugated anti-C3, yielded only minor variations in optical density per nanogram of C3, i.e. ±20 percent. In contrast to many ELISA systems, direct coupling of the antigen to the plate yielded far lower sensitivity as shown by the lower line represented by X's.

The ability of the anti-C3 antibodies employed in these studies to detect various forms and fragments of C3 were examined. For these experiments, purified C3, C3b, C3b dimers, C3bi, C3c, and C3d were substituted for C3 in the standard curve determination. The antibody detected C3, C3b, and C3b dimers with very similar dose response characteristics. Slightly less reactivity was observed with C3bi and C3c (50 to 70 percent of that produced by C3) while the antibody detected C3d poorly (approximately 10 percent of the optical density given by the same amount of C3).

Figure 2:
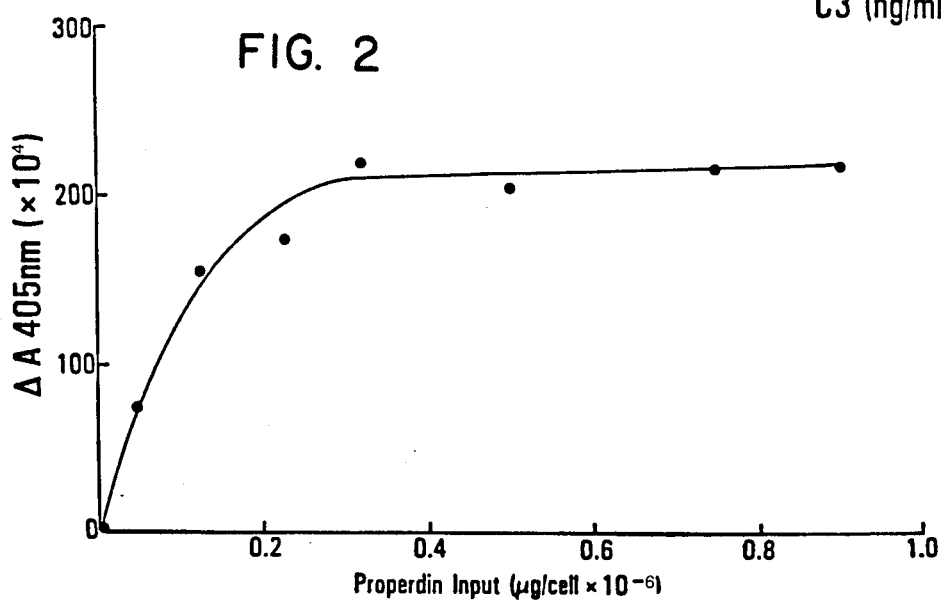
FIG. 2 is a graph showing the requirements for C3b and properdin on the same particle for reactivity in an ELISA. Varying amounts of activated properdin were incubated with EC3b. After washing, the cells were examined for ELISA reactivity.

Validity of Alternative Pathway Measurements By The ELISA:

A number of different types of studies were carried out to ascertain the requirements for the modified ELISA and to show that it specifically measured C3b and properdin deposition mediated by activation of the alternative pathway. In order to show a requirement for both C3b and properdin on the same particle for reactivity in the ELISA, $E_s$ bearing C3b were reacted with varying amounts of activated properdin. After washing, the cells were examined in the ELISA. As shown in FIG. 2, reactivity in the ELISA correlated with the amount of properdin added to the EC3b cells up to a plateau of reactivity at which point the cells are saturated with properdin.

Figure 3:
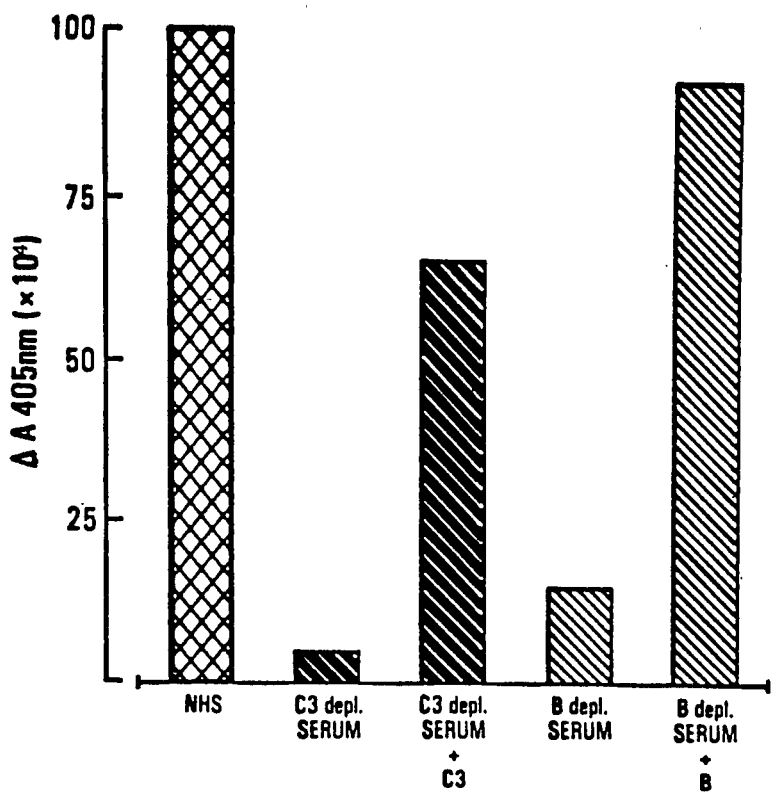
FIG. 3 is a chart showing the requirements for C3 and factor B for ELISA reactivity. E. coli 04 were incubated with normal serum, C3 depleted serum, reconstituted C3 depleted serum, factor B depleted serum and reconstituted factor B depleted serum. The reaction mixtures were then diluted and aliquots examined for reactivity in the ELISA.

Requirements for the proteins of the alternative pathway were also ascertained by adding an alternative pathway activator, E. coli 04, to normal serum, to serum depleted of C3, to serum depleted of C3 and reconstituted with physiological levels of purified C3, to serum depleted of Factor B and to serum depleted of factor B and reconstituted with physiological levels of purified B. After incubation, the reaction mixtures were diluted and examined in the ELISA. As shown in FIG. 3, E. coli added with serum depleted of C3 or factor B failed to react in the ELISA. Reactivity was, however, regained after reconstitution of the missing component.

In other studies, preneutralization of the anti-C3 conjugate or the anti-P coated plates with an excess of purified C3 or native P (EDTA serum), respectively, abrogated ELISA reactivity. Also, a serum-activator reaction mixture (E. coli 04) preincubated with an excess of anti-P before addition to the microtiter wells did not react in the ELISA (not shown).

Figure 4:
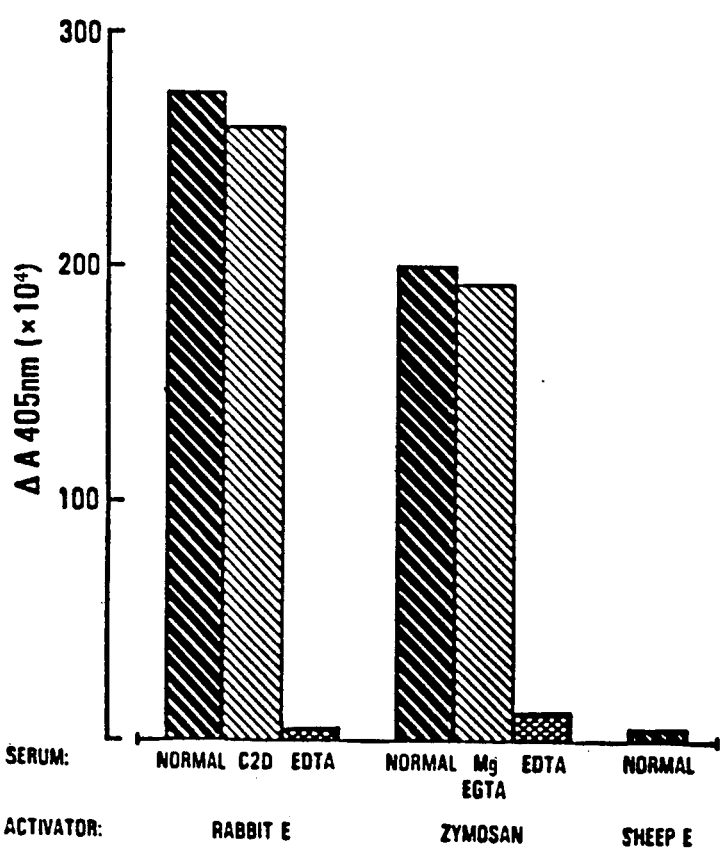
FIG. 4 is a chart showing the requirements for the alternative activation pathway for ELISA reactivity. $E_R$, zymosan or $E_S$ were incubated with normal serum, C2 deficient human serum, MgEGTA-NHS or with EDTA-NHS. The mixtures were then diluted and examined in the ELISA.

The next series of studies were for the purpose of determining whether integrity of the alternative activation pathway was required for reactivity in the ELISA. $E_R$ and zymosan were reacted with C2 deficient serum, MgEGTA-NHS or EDTA-NHS. As shown in FIG. 4, normal serum, C2 deficient serum and MgEGTA-NHS (thus lacking calcium required for the classical pathway) supported full ELISA reactivity with both activators whereas EDTA-NHS (lacking also magnesium, needed for both pathways) did not. In comparable studies, C4 depleted serum and MgEGTA-NHS supported full reactivity with $E_R$ and with E. coli K. 12 (not shown). Similarly, C2 deficient serum and normal serum yielded comparable ELISA values after reaction with zymosan. EDTA invariably abrogated ELISA reactivity. $E_s$, a non-activator, failed to engender ELISA reactivity after incubation in serum.

Figure 5:
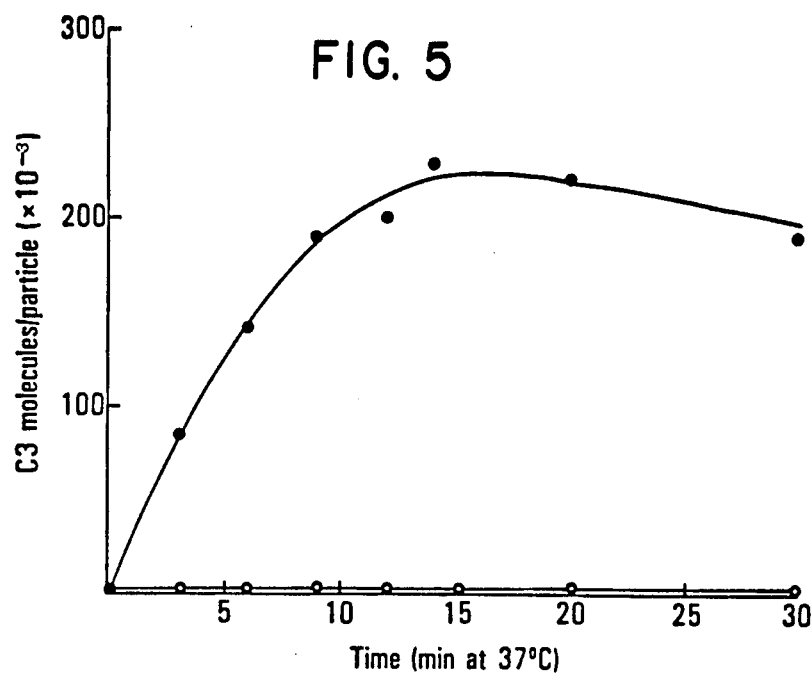
FIG. 5 is a graph showing the affects of the conversion of $E_S$ into alternative pathway activators by treatment with neuraminidase. $E_S$ designated by the circles, and neuraminidase treated $E_S$ designated by the dots, were incubated with MgEGTA-NHS. Samples were taken at intervals and centrifuged through a cushion of sucrose. The produced cell pellets were resuspended and examined in the ELISA. The optical densities measured were converted into bound C3b molecules per cell by reference to the C3 standard curve shown in FIG. 1.

In another approach, the effect of treatment of $E_s$ with neuraminidase, a procedure known to convert $E_s$ into alternative pathway activators, was examined. See Pangburn et al, *Proc. Natl. Acad. Sci. USA*, 75:2416 (1978). Untreated and neuraminidase treated $E_s$ were incubated with MgEGTA-NHS, and periodic samples were layered over cushions of sucrose and centrifuged. The $E_s$ pellets were examined for ELISA reactivity. As shown in FIG. 5, neuraminidase treatment rendered $E_s$ (represented by the dots) reactive in the ELISA while untreated $E_s$ (represented by the circles) did not react. Maximal C3b binding was observed after 15 minutes of incubation of the neuraminidase treated $E_s$ with MgEGTA-NHS, confirming the conversion of the cells into alternative pathway activators.

Comparison of The Modified ELISA With Measurements Of Radiolabeled C3b Deposition On The Activator:

Two alternative pathway activators $E_R$ and *K. pneumoniae*, and a non-activator, $E_s$, were incubated with MgEGTA-NHS containing radiolabeled C3. Replicate samples of the reaction mixtures were taken at intervals, layered over cushions of sucrose, centrifuged, and the pellets examined for modified ELISA reactivity and for radiolabeled C3b binding. Values were expressed as C3b molecules per particle.

Figure 6:
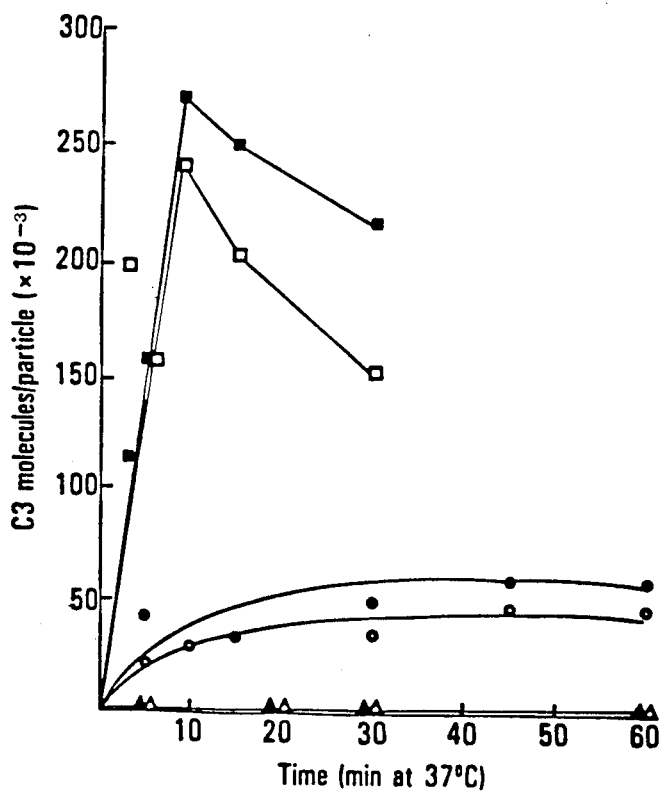
FIG. 6 is a graph showing a comparison of the ELISA with measurements of radiolabeled C3b deposition. $E_R$, K. pneumoniae and $E_S$ were incubated with MgEGTA-NHS containing radiolabeled C3. Samples taken at intervals were layered over sucrose cushions and centrifuged. The resulting pellets were assayed (a) for radioactivity, and after resuspension, (b) by the ELISA. Values were converted to C3b molecules per particle as described in the section on Materials and Methods below. The upper two curves were obtained with $E_R$ with radiolabeled C3 measurements designated by the solid squares and ELISA results designated by the open squares. The center two curves were obtained with *K. pneumoniae* with radiolabeled C3 measurements designated by the dots and ELISA results designated by the circles. The lower curves were obtained with $E_s$, with radiolabeled C3 measurements designated by the solid triangles and ELISA results designated by the open triangles.

As indicated in FIG. 6, measurements of alternative pathway activation by the modified ELISA and by radiolabeled C3b deposition exhibited parallel kinetic behavior. The upper two curves were obtained for $E_R$ with radiolabeled C3 measurement represented by the solid squares and modified ELISA represented by the open squares. The center two curves were obtained with *K. pneumoniae* for radiolabeled C3 measurements represented by the dots and ELISA results represented by the circles. The lower curves were obtained with $E_s$ with radiolabeled C3 measurements represented by the solid triangles and ELISA results represented by the open triangles.

The numbers of bound C3b molecules per particle measured with the two approaches were similar. Both methods also gave comparable parallel results with other activators including several gram negative bacteria and neuraminidase treated $E_s$ (not shown). $E_s$ were non-reactive as shown by the lower curves.

Use Of The Modified ELISA To Compare The Purified Alternative Pathway Proteins With MgEGTA-NHS As Sources Of The Alternative Pathway:

$E_R$, *K. pneumoniae* and $E_s$ were incubated with the purified alternative pathway proteins (PAP) and with MgEGTA-NHS. Periodically obtained replicate samples were centrifuged through sucrose and the pellets analyzed by the ELISA. Values were converted to C3 molecules per particle as described above.

Figure 7:
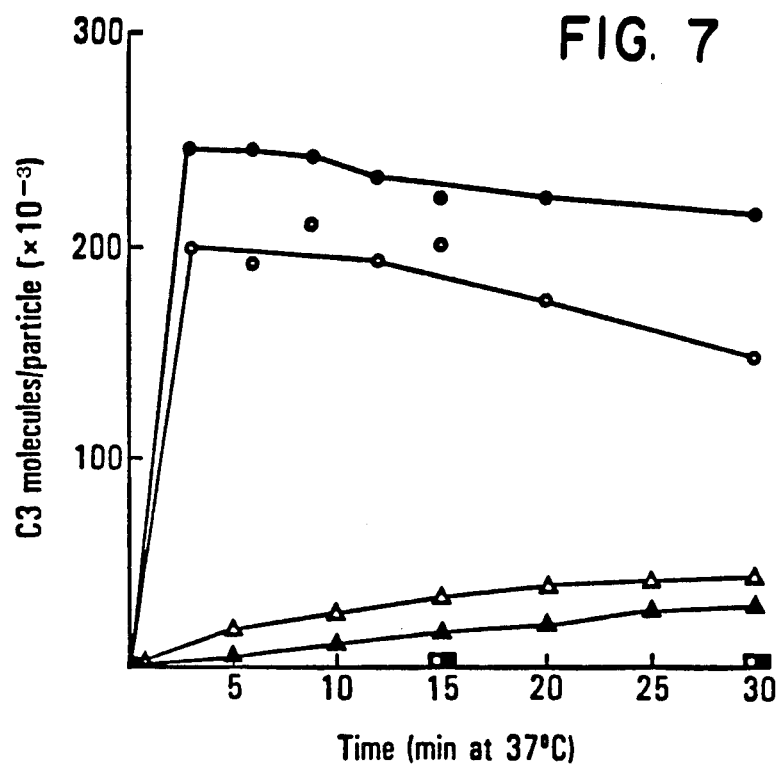
FIG. 7 is a graph showing the use of the ELISA to compare MgEGTA-NHS with PAP. $E_R$, *K. pneumoniae* and $E_s$ were incubated with MgEGTA-NHS and with PAP. Replicate samples were taken at intervals, centrifuged and the pellets resuspended and assayed in the ELISA. The upper two curves were obtained with $E_R$ as the activator with MgEGTA-NHS results designated by the circles, and PAP results designated by the dots. The center two curves were obtained with *K. pneumoniae* with MgEGTA-NHS results designated by the open triangles and PAP results designated by the solid triangles. The lower curves were obtained with $E_s$ with MgEGTA-NHS designated by the open squares and PAP designated by the solid squares.

The upper curves of FIG. 7 were obtained with rabbit erythrocytes, $E_R$, as the activator in solutions containing MgEGTA-NHS represented by the circles and PAP represented by the dots. The center two curves were obtained with *K. pneumoniae* as the activator in solutions of MgEGTA-NHS represented by the open triangles and PAP represented by the solid triangles. The lower curves were obtained with sheep erythrocytes, $E_S$, as the activator in solutions of MgEGTA-NHS represented by the open squares and PAP represented by the solid squares.

As can be seen in FIG. 7, the two sources of the alternative pathway exhibited parallel kinetic characteristics. The PAP gave somewhat higher values than MgEGTA-NHS with $E_R$ as the activator, while this relationship was reversed with *K. pneumoniae*. $E_s$ were not reactive in the ELISA with either alternative pathway source.

Figure 8:
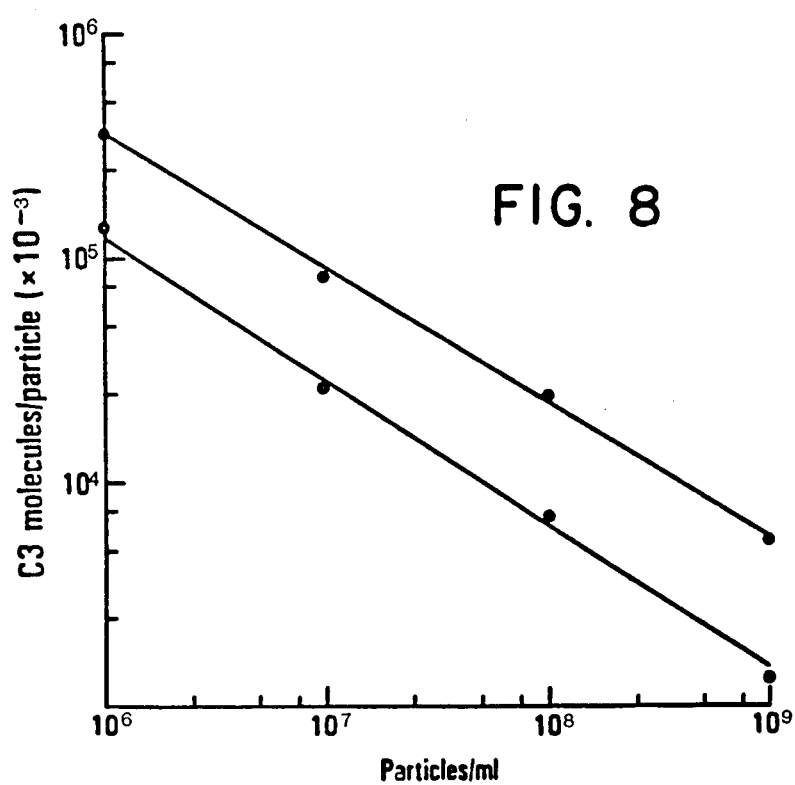
FIG. 8 is a graph showing the relationship between activator dose and reactivity in the ELISA. Varying numbers of $E_R$ and *K. pneumoniae* were incubated with MgEGTA-NHS. After 10 and 20 minutes for $E_R$ and *K. pneumoniae*, respectively, the mixtures were diluted and aliquots tested in the ELISA. $E_R$ results are designated by the dots and *K. pneumoniae* results are designated by the circles.

Parameters of The Alternative Pathway Modified ELISA:

Dose response studies were performed with varying numbers of $E_R$ and *K. pneumoniae*. After incubation with a constant amount of MgEGTA-NHS for 10 minutes ($E_R$) or 20 minutes (*K. pneumoniae*), the mixtures were diluted, and aliquots were assayed in the ELISA. As shown in FIG. 8 with $E_R$ represented by the dots and *K. pneumoniae* represented by the circles, ELISA reactivity was dose dependent.

The effect of different amounts of the activator on the kinetics of the reaction with MgEGTA-NHS was also examined. Several concentrations of $E_R$ ($10^7$, $10^{10}$, and $10^9$/milliliter) were incubated with a constant amount of MgEGTA-NHS. Samples taken at intervals were diluted, and aliquots were examined for ELISA reactivity. The family of curves obtained were parallel and demonstrated peak reactivity at 5 minutes followed by a gradual decline (not shown).

The stability of the ELISA reactive complexes generated with alternative pathway activation was also examined. MgEGTA-NHS was incubated with zymosan for one hour at 37 degrees C. after which EDTA was added to prevent further activation. Incubation was continued at 37 degrees C. Samples taken at intervals over the next 24 hours were diluted and assayed by the ELISA. At the one hour time point, 300 nanograms/milliliter of C3b were detected by the ELISA. Reactivity declined very slowly with first order kinetics at a rate of 1.25 percent per hour over the next 24 hours.

Simultaneous C3 hemolytic measurements were also performed. At the one hour time point, hemolytically active C3 in the serum had been depressed to 30 percent of the initial value; thereafter C3 hemolytic activity declined with first order kinetics at a rate of approximately 2.5 percent per hour.

In similar studies, serum incubated alone for several hours at 37 degrees C. became reactive in the ELISA. Only a minor proportion of the serum C3 (0.007 percent) was involved in this spontaneous activation reaction at the time of maximal reactivity (6 hours). After this time, reactivity was lost with first order kinetics, at a rate of 1.25 percent per hour. C3 hemolytic function in the spontaneously activated serum was lost with first order kinetics at a rate of 2.5 percent per hour.

Figure 9:
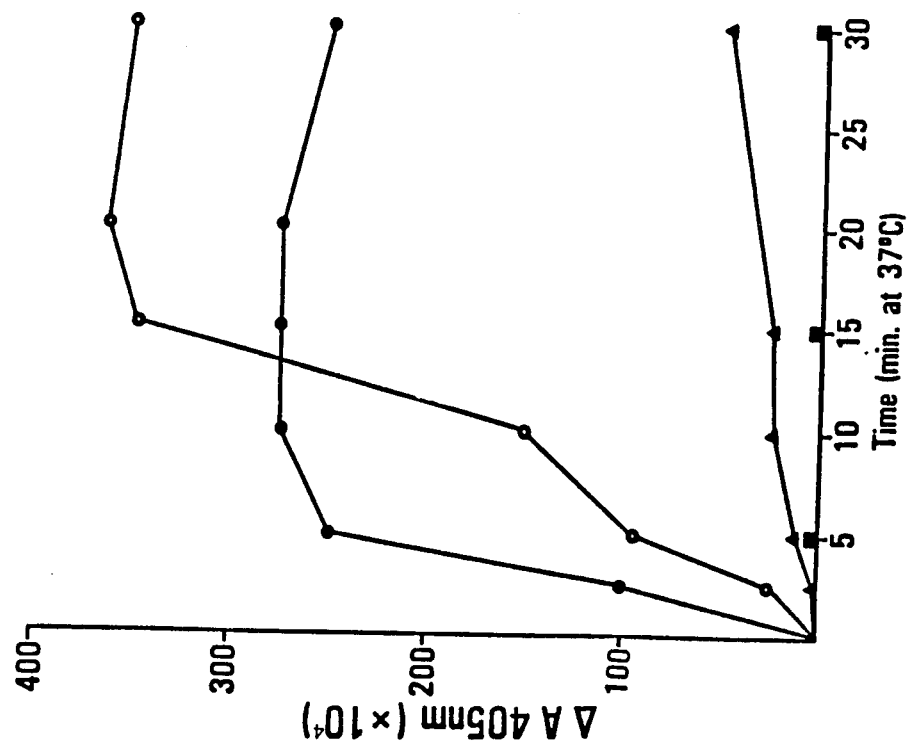
FIG. 9 is a graph showing the relationship between activator and time of peak reactivity in the ELISA. $E_R$, *K. pneumoniae* and Raji cells were incubated with MgEGTA-NHS. Samples were taken at intervals, diluted and aliquots examined in the ELISA. $E_R$ results are designated by the dots, *K. pneumoniae* results are designated by the circles, Raji cell results are designated by the triangles, and $E_s$ results are designated by the squares.

Measurement of Activation Kinetics With Strong, Moderate And Weak Alternative Pathway Activators:

Activation kinetics were measured with $E_R$, $E_S$, Raji cells and *K. pneumoniae*. The particles were incubated with MgEGTA-NHS and the mixtures sampled at intervals, diluted and aliquots were examined in the ELISA. As shown in FIG. 9, peak reactivities were: $E_R$ represented by the dots at 5–10 minutes; *K. pneumoniae* represented by the circles at 15–20 minutes; and Raji cells represented by the triangles at more than 30 minutes. $E_S$, represented by the squares, were not reactive.

Applications and Utility of The Alternative Pathway Modified ELISA:

The great sensitivity of the ELISA permits the study of very low levels of alternative pathway activation not readily quantified by other techniques. For instance, the ELISA can be used to detect alternative pathway activation by particles as small as viruses. In these studies, Epstein-Barr, influenza, and Moloney leukemia viruses were incubated either with normal human serum (NHS) or with MgEGTA-NHS. After 20 minutes at 37 degrees C., the mixtures were diluted and aliquots were examined in the ELISA. All three viruses activated the alternative pathway as shown by the generation of ELISA reactivity after incubation in MgEGTA-NHS. The results are shown below in Table I.

TABLE I

REACTIVITY OF VARIOUS ACTIVATORS IN THE ALTERNATIVE PATHWAY ELISA

| ACTIVATOR** | Change in Absorbence at 405 nm × ($10^4$) | |
|---|---|---|
| | NHS | MgEGTA-NHS |
| Epstein-Barr Virus | 301 (2000)* | 142 (500) |
| Influenza WS/33 Virus | 100 (500) | 45 (200) |
| Moloney Leukemia Virus | 156 | 58 |
| Calf Thymus DNA | 100 | 73 |
| Zymosan (1:2 Serum) | 193 | 187 |
| Zymosan (1:8 Serum) | 124 | 3 |
| Immune Complexes (1:2 Serum) | 100 | 88 |
| Immune Complexes (1:8 Serum) | 42 | 0 |
| Heparin | 5 | 7 |
| EA | 12 | 10 |

*Values in parentheses denote bound C3b molecules/virion.
**Concentrations given above, see General Procedure For Testing Samples For The Modified ELISA.

The ELISA can also be used to analyze reaction mechanisms of the alternative pathway. For example, in the present studies we have observed ELISA reactivity engendered secondary to activation of the classical pathway by some, but not other classical pathway activators. For example, the non-immune classical pathway activators Moloney leukemia virus and DNA triggered the amplification loop with properdin recruitment as manifested by reactivity in the ELISA after incubation in normal serum (Table I). Classical pathway activation leading to alternative pathway activation with properdin recruitment was also demonstrated by adding zymosan and human immune complexes to serum if the serum was first diluted to abrogate reactivity of the alternative pathway (Table I). Other classical pathway activators such as erythrocyte amboceptor (EA) and heparin incubated with normal serum failed to recruit the alternative pathway (Table I). Classical pathway reactivity by Moloney leukemia virus, DNA, zymosan, immune complexes, EA and heparin, was independently verified in these studies.

Figure 10:
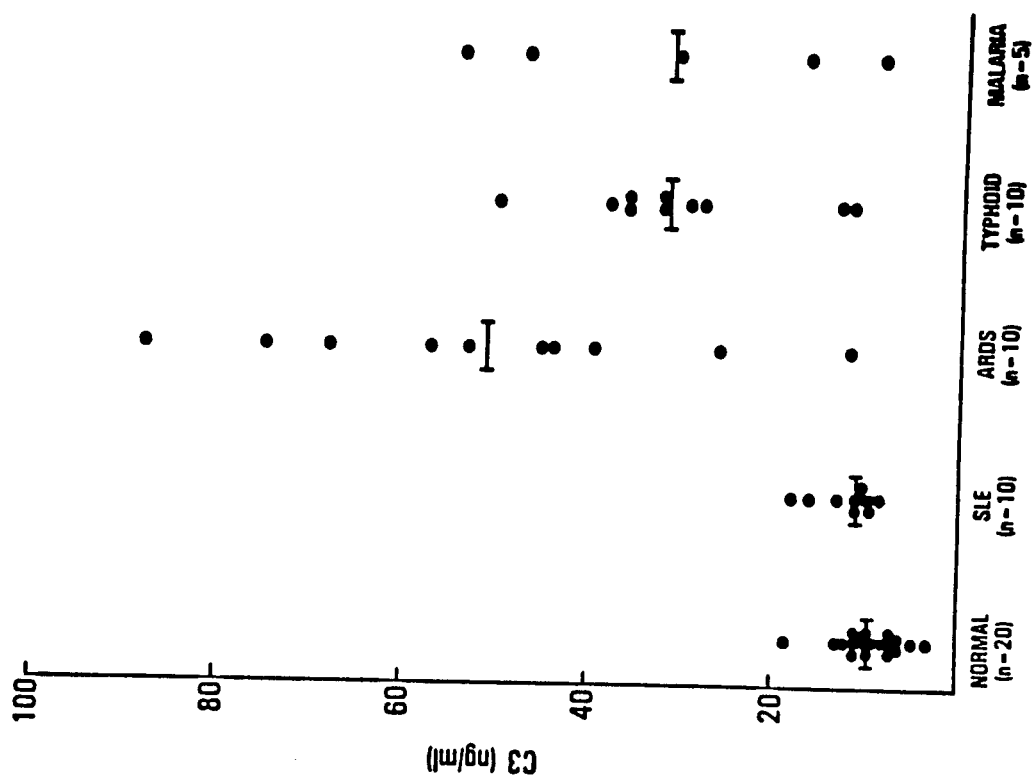
FIG. 10 is a graph showing the results of testing clinical sera. Serum or plasma samples from patients with diagnoses of SLE, ARDS, typhoid fever, or malaria were diluted and examined in the ELISA. The horizontal bars represent the mean value for each type of sample.

Detection of Alternative Pathway Activation In Clinical Sera With The Modified ELISA:

The stability of the ELISA-reactive complexes permits the ELISA to be used to examine clinical sera. Sera from 10 individuals with systemic lupus erythematosus (SLE) were either not reactive or only marginally reactive in the alternative pathway ELISA as shown in FIG. 10. The bars represent mean values. See also Table II below. However, most of the sera tested from patients with the adult respiratory distress syndrome (ARDS), typhoid fever, and malaria were positive with the ARDS patients exhibiting the highest levels.

TABLE II

ELISA REACTIVITY OF HUMAN SERA

| Patients for Serum Source | Amounts of CS Detected (ng/ml) |
|---|---|
| Normal Human Sera (20 patients) | 0–10 |
| Sera From Patients With SLE | |
| 1 | 10 |
| 2 | 12 |
| 3 | 10 |
| 4 | 11 |
| 5 | 17 |
| Sera From Patients With ARDS | |
| 1 | 53 |
| 2 | 45 |
| 3 | 75 |
| 4 | 13 |
| 5 | 57 |
| 6 | 39 |
| 7 | 88 |
| 8 | 44 |
| 9 | 68 |
| 10 | 26 |
| Sera From Patients With Typhoid Fever | |
| 1 | 36 |
| 2 | 29 |
| 3 | 12 |
| 4 | 50 |
| 5 | 36 |
| 6 | 13 |
| 7 | 32 |
| 8 | 28 |
| 9 | 32 |
| 10 | 38 |
| Sera From Patients With Malaria | |
| 1 | 54 |
| 2 | 31 |
| 3 | 9 |
| 4 | 47 |
| 5 | 17 |

The Use Of Modified ELISA For Detecting Alternative Pathway Activation

The studies discussed above describe and validate a new, specific and highly sensitive ELISA for the detection and quantification of activation of the alternative complement pathway in human serum. Reactivity in the alternative pathway ELISA is dependent on the dual presence of properdin and a C3 derivative on the same activating particle or complex. Integrity of the alternative pathway and magnesium were also required for ELISA reactivity (FIGS. 2-4). In a series of studies to validate the ELISA, $E_s$ were converted to alternative pathway activators by treatment with neuraminidase (FIG. 5), and the kinetics of alternative pathway activation assessed with the ELISA were identical to those observed in another technique used to measure activation, deposition of radiolabeled C3b (FIG. 6). The numbers of bound C3b molecules measured by the two approaches were also similar although the ELISA values were slightly lower. This difference, which is not considered significant, may be due to inaccessibility of some of the activator-bound C3b molecules to the enzyme labeled anti-C3, although other explanations are also possible.

In other studies the ELISA was used to compare MgEGTA-NHS and the PAP as sources of the alternative pathway. The two sources of alternative pathway proteins produced identical activation kinetics with several activators (FIG. 7). Differences in the numbers of bound C3b molecules were detected, however. Thus, with $E_R$ as the activator, the ELISA detected more bound C3b molecules per cell when the PAP was used as compared to MgEGTA-NHS, while the converse was observed with *K. pneumoniae* as the activator.

The time of maximal reactivity detected by the ELISA also correlated with the strength of the alternative pathway activator as assessed by an independent measure of activation, the restriction index (R.I.). See Pangburn et al., *Proc. Natl. Acad. Sci. USA.*, 75:2416 (1978). The R.I. refers to the ratio of bound factor H to bound C3b molecules as tested in a model system with radiolabeled proteins. It is therefore an inverse measure of activator strength.

Thus, a strong activator such as $E_R$ with an R.I. of about 0.1 gave rapid kinetics and peak reactivity in the ELISA occurred after 5 to 10 minutes of incubation. Moderate activators, such as *E. coli* 04, *K. pneumoniae* and neuraminidase treated $E_s$ with an R.I. values of about 0.3 showed intermediate kinetics in the ELISA with peak reactivity occurring after 15 to 30 minutes of incubation. Weak activators such as Raji cells with an R.I. of about 0.6 exhibited peak activity after 30 minutes of incubation. An even longer period of time (6-8 hours) was required to reach peak reactivity with the "spontaneous" activation reaction.

The modified ELISA of this invention provides a considerable advantage over other alternative pathway activation assays. For example, alternative pathway mediated lysis of $E_R$ measures residual functional activity of the pathway and not activation, and lysis is a secondary event dependent also on the integrity of the membrane attack pathway. Certain other approaches either based on measurement of individual protein levels, conversion products, or assessment of the functional integrity of the pathway can provide evidence that activation has occurred, but these tests do not directly measure the activation events.

The only currently available approach to directly detect and quantify activation depends on the binding of radiolabeled properdin, C3b, factor B, factor H, or combinations thereof to activators. The ELISA has a major advantage over such tests by not requiring the purified proteins in functionally active radiolabeled form. Such assays also require relatively large numbers of activator particles in order to bind sufficient amounts of radioactivity for quantitative measurements. This is particularly true with serum to which radiolabeled components have been added as the radiolabel is diluted with large amounts of unlabeled component under such conditions.

The modified ELISA of this invention has a number of other major advantages. Among these is great sensitivity. For example, 10-20 nanograms/milliliter of C3b deposited together with properdin on an activator are readily measureable as shown in FIG. 1. That value corresponds to approximately 0.0015 percent of the C3 in serum. This great sensitivity permits the analysis of minor degrees of alternative pathway activation not previously detectable. Thus, "spontaneous" activation can be quantified and studied. The sensitivity also allows, for the first time, the study of alternative pathway activation by activators or particles available in only limited amounts, such as viruses (Table I).

Great sensitivity is an intrinsic property of enzyme immunoassays, many of which are comparable to radioimmunoassays in this regard. This is particularly true of the system of the present invention. The modified ELISA uses antibodies to two different constituent proteins of an activated complex. This gives it extreme specificity coupled with negligible background reactivity. In this context, even small amounts of color are significant.

Studies with the modified ELISA of this invention revealed complexities in the reaction mechanism of the alternative pathway which merit further investigation. For example, several activators including several viruses, DNA, zymosan and immune complexes activated the classical pathway leading to secondary triggering of the amplification loop with recruitment of properdin. In contrast, other classical pathway activators such as EA and heparin failed to activate the amplification loop. Another example is the appearance of extremely stable ELISA reactive complexes in the supernatant of mixtures of serum with certain activators, such as zymosan and *K. pneumoniae* but not with other activators such as $E_R$. The nature of the complexes bearing C3 and P determinants is unknown. Among possible candidates are P,C3b complexes, eluted from the activator, possibly attached to fragments of the activator, or eluted activated P which would have the ability to directly interact with C3b in the supernatant.

The ELISA of the present invention is eminently suitable for clinical use. The required antisera to properdin and to C3 are available commercially. Affinity purification of the antisera can be accomplished without isolation of properdin and C3. Among several procedures to accomplish this goal is absorption of the antibodies to zymosan which had been pre-reacted with normal serum, followed by elution and *Staphylococcus aureus* protein A chromatography.

Yet another advantage of the alternative pathway ELISA of this invention is that it may be utilized to detect and quantify activation which has already occurred, since the properdin and C3b bearing complexes are extremely stable. This allows its use with clinical sera as shown in Table II and FIG. 10. Thus, the progress of a patient under treatment may be determined by the amount of alternative pathway activation observed over the period of treatment. The utility is further expanded by the stability of the C3b,P complexes measured by the assay. Thus, stored sera or plasma and samples collected under less than optimal conditions can be studied.

Although the sera from patients with SLE were negative or marginally reactive in the alternative pathway ELISA, the same sera showed evidence of marked classical pathway activation (markedly reduced CH50 levels). This finding is in accord with current concepts of the primary role of immune complexes and the classical pathway in SLE. See Aguado, et al., *Clin. Exp. Immunol.*, 42:495–505 (1980).

Some of the sera from patients with typhoid fever and with malaria were moderately reactive in the alternative pathway ELISA while other sera were not. Parallel studies of the same samples using a recently developed classical pathway ELISA showed all of the typhoid fever samples and several of the malaria samples, and had evidence of marked C1 activation. See Harpel et al., *Clin. Res.*, 30:563A (1982).

Most of the 10 sera from ARDS patients were quite reactive in the alternative pathway ELISA. In contrast, 8 of these sera were negative, and 2 were only marginally reactive in the classical pathway ELISA. These findings with the ARDS sera are in accord with indications of the involvement of the alternative pathway in this condition.

The foregoing is intended as illustrative of the present invention but not limiting. Numerous variations and modifications may be effected without departing from the true spirit and scope of the novel concepts of the invention.

What is claimed is:

1. An assay method for an activated complex of the complement system comprised of a first complement component of the complex and second complement component of the complex the assay method to be performed on a sample and comprising the steps of:
   binding a first specific binding agent to any first complement component forming part of the complex present in the sample;
   binding a second specific binding agent to any second complement component forming part of the complex, the second specific binding agent including a label, the first and second specific binding agents bound to the complex forming an aggregate; and
   determining the presence of label bound as part of the aggregate.

2. The assay method of claim 1 wherein either the first complement component or the second complement component is properdin.

3. The assay method of claim 1 wherein the first complement component is properdin.

4. The assay method of claim 3 wherein the first specific binding agent includes an anti-properdin antibody.

5. The assay method of claim 1 wherein either the first complement component or the second complement component is C3b.

6. The assay method of claim 1 wherein the second complement component is C3b.

7. The assay method of claim 6 wherein the second specific binding agent includes an anti-C3b antibody.

8. The assay method of claim 1 wherein the first specific binding agent includes a functional idiotype-containing polypeptide.

9. The assay method of claim 1 wherein the second specific binding agent includes a functional idiotype-containing polypeptide.

10. The assay method of claim 1 including the additional step of separating any second specific binding agent not forming part of the aggregate from the aggregate prior to determining the presence of label bound as part of the aggregate.

11. The assay method of claim 10 wherein the first specific binding agent is immobilized.

12. The assay method of claim 11 wherein the sample is first contacted with immobilized first specific binding agent and any portion of the sample which does not bind with the first specific binding agent is removed before the second specific binding agent is bound to the complex.

13. The assay method of claim 12 wherein any label-containing second specific binding agent not part of the aggregate is removed by washing.

14. The assay method of claim 10 wherein the first specific binding agent is coupled to a separation means for enhancing the separation of the aggregate from second specific binding agent not forming part of the aggregate.

15. The assay method of claim 14 wherein the separation means is a carrier.

16. The assay method of claim 14 wherein the separation means is a solid matrix.

17. The assay method of claim 1 wherein either the first complement component or the second complement component is factor B.

18. The assay method of claim 1 wherein either the first complement component or the second complement component is C4b.

19. The assay method of claim 1 wherein either the first complement component or the second complement component is C2a.

20. The assay method of claim 1 wherein the first complement component and the second complement components are selected independently from the group consisting of C5b, C6, C7, C8, and C9.

21. The assay method of claim 1 wherein second specific binding agent not part of the aggregate is separated by a molecular weight-size selective process.

22. The assay method of claim 1 wherein the label is an enzyme.

23. The assay method of claim 22 wherein the first specific binding agent is immobilized to form an enzyme-linked immunosorbent assay.

24. The assay method of claim 1 wherein a predetermined amount of sample is used and the amount of label-including second specific binding agent bound to the aggregate is measured.

25. An assay method for quantifying complement system activation in a body fluid, the method comprising the steps of:
   (a) contacting a predetermined amount of body fluid with an immobilized first antibody specific to a first complement component such that the first antibody binds with any first complement component present in the body fluid that forms part of an activated complex including a second complement component, the presence of the complex in the body fluid indicating complement system activation;
   (b) contacting the complex with a second antibody linked to a label and specific to the second complement component such that the second antibody binds with the second complement component forming part of complex to link the label to the complex; and
   (c) measuring the quanity of label linked to the complex.

26. The assay method of claim 25 including the additional step of removing label not linked to the complex before measuring.

27. The assay method of claim 26 wherein label-linked second antibody not bound to the complex is removed by washing.

28. The assay method of claim 25 wherein alternative pathway activation is quantified and presence of the complex is indicative of alternative pathway activation.

29. The assay method of claim 28 wherein the first complement component is properdin and the first antibody is an anti-properdin antibody.

30. The assay method of claim 26 wherein the body fluid is serum.

31. The assay method of claim 26 wherein the label is an enzyme.

32. The assay method of claim 26 wherein the second complement component is C3b and the second antibody is anti-C3b antibody.

33. The assay method of claim 26 wherein the body fluid is contacted with the first antibody before the complex is contacted with the second antibody.

34. The assay method of claim 26 wherein the complex is contacted with the second antibody before the body fluid is contacted with the first antibody.

35. The assay method of claim 25 further including the steps of providing a known quantity of second complement component immobilized separately from the first antibody, contacting the immobilized second complement component with a separate quantity of the second antibody linked to the label such that the second antibody binds with the immobilized second complement component, measuring the quantity of label linked to the immobilized second complement component as a reference standard, and comparing the quantity of label-linked second antibody bound to the complex with the measured quantity of label of the reference standard.

36. An assay method for quantifying alternative complement pathway activation in a serum sample comprising the steps of:
(a) immobilizing a functional anti-properdin idiotype-containing polypeptide on a solid matrix;
(b) linking a labelling enzyme to a functional anti-C3b idiotype-containing polypeptide;
(c) contacting a predetermined amount of serum sample with the immobilized anti-properdin polypeptide such that any activated complex comprising properdin and C3b present in the serum sample binds with the anti-properdin polypeptide;
(d) contacting the labeled anti-C3b polypeptide with the complex such that the labeled anti-C3b polypeptide binds to the complex and links the labeling enzyme to the complex;
(e) removing labelling enzyme not linked to the activated complex; and
(f) measuring the amount of labelling enzyme remaining linked to the complex.

37. The assay method of claim 36 wherein the sample is contacted with the anti-properdin polypeptide before the anti-C3b polypeptide is contacted with the complex.

38. The assay method of claim 36 further comprising the steps of immobilizing a known quantity of C3b separately from the anti-properdin polypeptide, contacting a separate quantity of labeled anti-C3b polypeptide with the immobilized C3b such that the labeled anti-C3b polypeptide binds to the immobilized C3b, removing any labeled anti-C3b polypeptide not bound to the immobilized C3b, measuring the amount of label linked to the immobilized C3b as a reference standard, and comparing the measurement label linked to the complex with the reference standard.

39. A diagnostic assay system for determining the presence an activated complex of the complement system including a first complement component and a second complement component in a sample, the system comprising in kit form:
(a) a first specific binding agent specific to the first complement component;
(b) a second specific binding agent specific to the second complement component and including a label; when contacted with the complex in the sample to be assayed, the first and second specific binding agents individually binding to and forming an aggregate with the complex, such that the aggregate so formed is separable from any second specific binding agent that is not part of the aggregate.

40. The assay system of claim 39 further including a solid matrix on which the first specific binding agent can be immobilized.

41. The assay system of claim 39 including a separation means coupled to the first specific binding agent for enhancing separation of the aggregate from second specific binding agent not part of the aggregate.

42. The assay system of claim 41 wherein the separation means is a carrier.

43. The assay system of claim 39 wherein the specific binding agents each include an idiotype-containing polypeptide.

44. The assay system of claim 43 wherein the second specific binding agent includes an anti-C3b antibody.

45. The assay system of claim 43 wherein the first specific binding agent includes an anti-properdin antibody.

46. The assay system of claim 39 wherein the label is an enzyme.

47. A diagnostic assay system for determining the activation of the complement system by the presence in a body fluid sample of an activated complex including a first complement component and a second complement component, the system comprising in kit form:
(a) a first antibody to the first complement component of the complex coupled to a solid matrix; and
(b) a solution containing a second antibody to the second complement component of the complex and linked to a label; when contacted with the complex, the coupled first antibody binding the first complement component of the complex and the second, label-linked antibody binding to the second complement component of the complex thereby forming an aggregate coupled to the solid matrix.

48. The assay system of claim 47 further including a separate standard reference having a known amount of immobilized second complement component.

49. The assay system of claim 47 wherein the second antibody is an anti-C3b antibody.

50. The assay system of claim 47 wherein the first antibody is an anti-properdin antibody.

51. The assay system of claim 47 wherein the label is an enzyme.

52. An aggregate for use in an assay method comprising:
(a) an activated complex indicative of activation of the complement system and comprising a first complement component and a second complement component;
(b) a first specific binding agent bound to the first component in the complex; and
(c) a second specific binding agent including a label bound to the second component in the complex.

53. The aggregate of claim 52 wherein complex includes C3b.

54. The aggregate of claim 52 wherein the complex includes properdin.

55. The aggregate of claim 52 wherein the label is an enzyme.

56. An aggregate for use in an assay method for indicating activation of the alternative complement pathway comprising:
(a) an activated complex including C3b and properdin;
(b) an anti-properdin antibody bound to the properdin in the complex; and
(c) a C3b antibody linked to a labelling enzyme and bound to the C3b in the complex.

* * * * *